(12) United States Patent
Dodda et al.

(10) Patent No.: US 9,796,695 B2
(45) Date of Patent: Oct. 24, 2017

(54) PROCESS FOR PREPARING BENZOFURAN-2-CARBOXAMIDE DERIVATIVES

(71) Applicant: SYMED LABS LIMITED, Hyderabad (IN)

(72) Inventors: Mohan Rao Dodda, Hyderabad (IN); Jithender Aadepu, Nalgonda (IN)

(73) Assignee: SYMED LABS LIMITED (IN)

( * ) Notice: Subject to any disclaimer, the term of this patent is extended or adjusted under 35 U.S.C. 154(b) by 0 days.

(21) Appl. No.: 15/597,695

(22) Filed: May 17, 2017

(65) Prior Publication Data

US 2017/0267655 A1    Sep. 21, 2017

Related U.S. Application Data

(62) Division of application No. 14/875,039, filed on Oct. 5, 2015, now Pat. No. 9,682,946, which is a division of application No. 14/410,198, filed as application No. PCT/IN2013/000404 on Jul. 1, 2013, now Pat. No. 9,399,630.

(30) Foreign Application Priority Data

Jul. 2, 2012 (IN) .......................... 2629/CHE/2012

(51) Int. Cl.
| | |
|---|---|
| C07D 405/12 | (2006.01) |
| C07D 307/85 | (2006.01) |
| C07D 209/10 | (2006.01) |
| C07D 209/12 | (2006.01) |
| C07D 401/12 | (2006.01) |

(52) U.S. Cl.
CPC ......... *C07D 307/85* (2013.01); *C07D 209/10* (2013.01); *C07D 209/12* (2013.01); *C07D 401/12* (2013.01); *C07D 405/12* (2013.01)

(58) Field of Classification Search
CPC .. C07D 405/12; C07D 307/85; C07D 209/10; C07D 209/12; C07D 401/12
See application file for complete search history.

(56) References Cited

U.S. PATENT DOCUMENTS

| | | | |
|---|---|---|---|
| 5,532,241 A | 7/1996 | Bottcher et al. | |
| 5,977,112 A | 11/1999 | Bathe et al. | |
| 8,575,161 B2 * | 11/2013 | Roche | C07D 307/85 514/233.5 |
| 9,315,456 B2 | 4/2016 | Dodda et al. | |
| 9,682,946 B2 | 6/2017 | Dodda et al. | |

FOREIGN PATENT DOCUMENTS

| | | |
|---|---|---|
| CN | 102267932 | 12/2011 |
| WO | 2014006637 A3 | 1/2014 |

OTHER PUBLICATIONS

International Search Report and Written Opinion of PCT/IN2013/000404 dated Mar. 21, 2014.
Patent Interference No. 106,075; *Symed Labs Limited (Dodda et al.)* v. *Alembic Pharmaceuticals Limited (Jayaraman et al.)* dated Apr. 18, 2017.

* cited by examiner

*Primary Examiner* — Sun Jae Yoo
(74) *Attorney, Agent, or Firm* — Caesar Rivise, PC

(57) ABSTRACT

Provided herein are novel, commercially viable and industrially advantageous processes for the preparation of benzofuran-2-carboxamide derivatives and their intermediates, or a pharmaceutically acceptable salt thereof, in high yield and purity. Provided particularly herein are novel, commercially viable and industrially advantageous processes for the preparation of vilazodone or a pharmaceutically acceptable salt thereof in high yield and purity. Provided also herein is an improved and commercially viable process for the preparation of 3-(4-hydroxybutyl)-1H-indole-5-carbonitrile, in high yield and purity, using novel intermediate compound 3-(4-hydroxybutyryl)-1H-indole-5-carbonitrile.

7 Claims, No Drawings

PROCESS FOR PREPARING BENZOFURAN-2-CARBOXAMIDE DERIVATIVES

CROSS REFERENCE TO RELATED APPLICATION

This application is a Divisional of Ser. No. 14/875,039, filed Oct. 5, 2015, which is a Divisional of Ser. No. 14/410,198, filed Dec. 22, 2014, now U.S. Pat. No. 9,399,630, issued Jul. 26, 2016, which is National Stage Entry of PCT/IN2013/000404, filed Jul. 1, 2013, which claims the benefit of priority to Indian Provisional Patent Application No. 2629/CHE/2012, filed on Jul. 2, 2012, all of which are incorporated herein by reference in their entireties.

FIELD OF THE INVENTION

The present invention relates to novel, commercially viable and industrially advantageous processes for the preparation of benzofuran-2-carboxamide derivatives and their intermediates, or a pharmaceutically acceptable salt thereof, in high yield and purity. The present invention particularly relates to novel, commercially viable and industrially advantageous processes for the preparation of vilazodone or a pharmaceutically acceptable salt thereof in high yield and purity. The present invention further relates to an improved and commercially viable process for the preparation of 3-(4-hydroxybutyl)-1H-indole-5-carbonitrile, in high yield and purity, using novel intermediate compound 3-(4-hydroxybutyryl)-1H-indole-5-carbonitrile.

BACKGROUND OF THE INVENTION

U.S. Pat. No. 5,532,241 (hereinafter referred to as the '241 patent) discloses a variety of piperidine and piperazine derivatives and their pharmaceutically acceptable salts, processes for their preparation, pharmaceutical compositions comprising the derivatives, and methods of use thereof. These compounds are active on the central nervous system, especially in terms of 5-$HT_{1A}$-agonist and 5-HT-reuptake inhibition. They are furthermore active as serotonin agonists and antagonists. These compounds and their physiologically acceptable acid addition salts can, therefore, be used as active ingredients for anxiolytics, antidepressants, antipsychotics, neuroleptics, and antihypertensives. Among them, Vilazodone hydrochloride, 5-[4-[4-(5-Cyanoindol-3-yl)butyl]piperazin-1-yl]benzofuran-2-carboxamide hydrochloride, is a serotonergic antidepressant that is used for the treatment of major depressive disorder (MDD). Vilazodone hydrochloride is represented by the following structural formula:

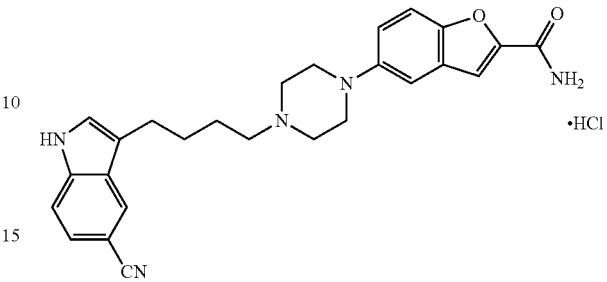

Vilazodone hydrochloride was approved by the FDA for use in the United States to treat major depressive disorder and it is sold under the trade name VIIBRYD™. It is orally administered as tablets containing 10 mg, 20 mg and 40 mg of vilazodone as the hydrochloride salt.

Various processes for the preparation of benzofuran-2-carboxamide derivatives, preferably vilazodone, their intermediate compounds, and their pharmaceutically acceptable salts are apparently disclosed in U.S. Pat. No. 5,532,241, U.S. Pat. No. 5,723,614, U.S. Pat. No. 5,977,112, U.S. Pat. No. 5,418,237 and U.S. Pat. No. 7,799,916; U.S. Patent Application Publication No. 2010/0036139A1; Chinese Patent Application Publication Nos. CN 102267932, CN 102267985, CN 102180868, CN 102796037, CN 102875538, CN 102659660 and CN102617558 and Journal of Medicinal Chemistry, 2004, Vol. 47, No. 19, pages 4684-4692; Drugs of the Future 2001, 26(3), 247, and Liebigs Ann. Chem. 1988, 749-752.

U.S. Pat. No. 5,532,241 (hereinafter referred to as the '241 patent) describes several synthetic routes for preparing vilazodone. According to one synthetic process, vilazodone is prepared by the condensation of 5-(1-pipearzinyl)benzofuran-2-carboxamide with 3-(4-chlorobutyl)-1H-indole-5-carbonitrile. According to another synthetic process, vilazodone is prepared by reacting 5-[4-[4-(5-cyano-1H-indol-3-yl)butyl]piperazin-1-yl]benzofuran-2-carboxylic acid with 2-chloro-1-methylpyridinium methanesulfonate in the presence of N-methylpyrrolidone to produce a reaction mass, followed by treatment with dried ammonia gas and subsequent working up to produce vilazodone. The synthetic routes are depicted in scheme 1:

Scheme 1:

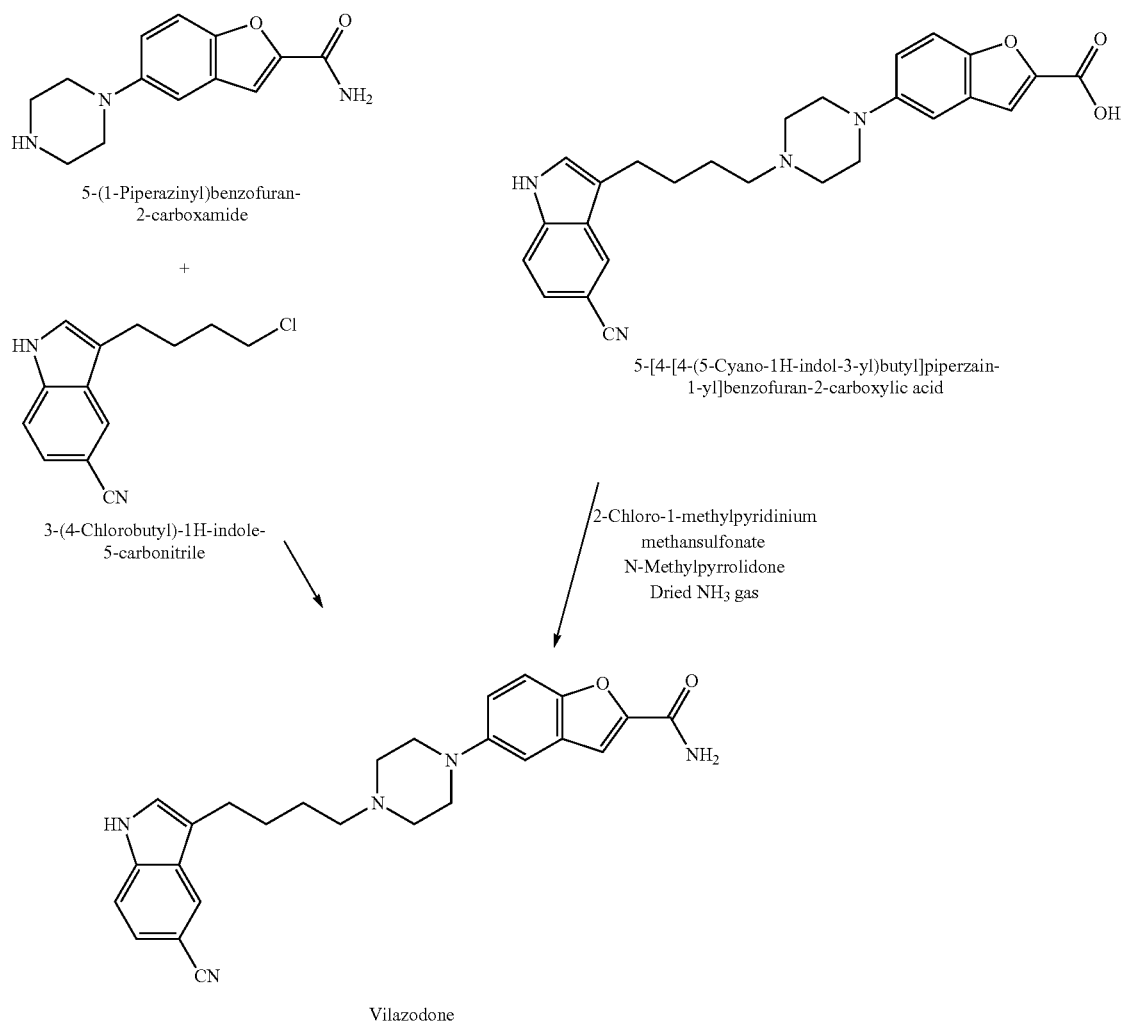

Similar process for the preparation of vilazodone is also reported in Journal of Medicinal Chemistry, 2004, Vol. 47, No. 19, pages 4684-4692 (hereinafter referred to as the 'JMC article'). As per the process reported in the JMC article (see column-1 of Page No. 4690), the vilazodone is prepared by reacting 5-[4-[4-(5-cyano-1H-indol-3-yl)butyl] piperazin-1-yl]benzofuran-2-carboxylic acid with 2-chloro-1-methylpyridinium iodide in the presence of N-methylpyrrolidone to produce a reaction mass, followed by drop wise addition of ethyldiisopropyl amine while introducing ammonia gas and subsequent work up to produce vilazodone. The resulting vilazodone free base is then converted into its hydrochloride salt by dissolving vilazodone free base in hot 2-propanol to form a solution, followed by slow addition of HCl-saturated 2-propanol at room temperature until complete precipitation occurs to yield vilazodone hydrochloride (Melting Point: 277-279° C.).

The 'JMC' Article also describes a process for the preparation of 3-(4-chlorobutyl)-1H-indole-5-carbonitrile as depicted in scheme 2:

Scheme 2:

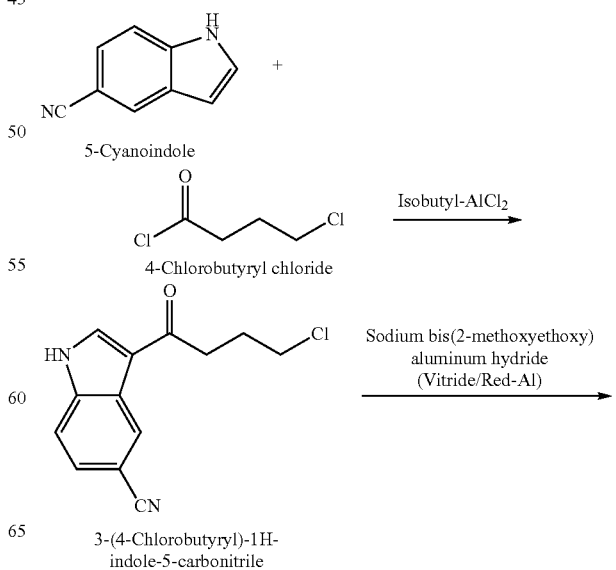

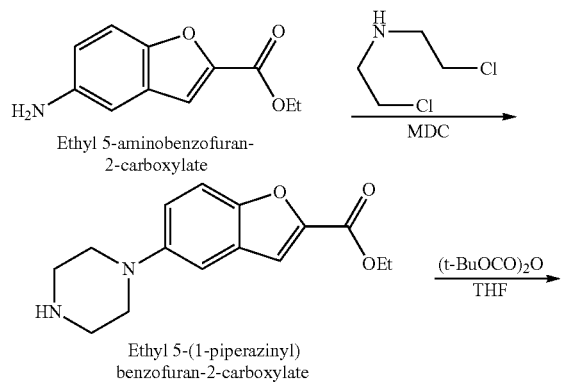

3-(4-Chlorobutyryl)-1H-
indole-5-carbonitrile

As per the process described in the JMC Article, 3-(4-chlorobutyl)-1H-indole-5-carbonitrile is prepared by reacting 5-cyanoindole with 4-chlorobutyryl chloride in the presence of isobutyl-AlCl$_2$ to produce 3-(4-chlorobutyryl)-1H-indole-5-carbonitrile, which is then subjected to selective deoxygenation of the keto function with sodium bis(2-methoxyethoxy)aluminum hydride (Vitride/Red-Al) to produce the 3-(4-chlorobutyl)-1H-indole-5-carbonitrile.

According to U.S. Pat. No. 5,418,237 (hereinafter referred to as the '237 patent) & the Research Article 'Drugs of the Future 2001, 26(3), 247', 3-(4-chlorobutyl)-1H-indole-5-carbonitrile is prepared by reacting 5-cyanoindole with 4-chlorobutyryl chloride to give 3-(4-chlorobutyryl)-1H-indole-5-carbonitrile, which then reduced with diborane to produce the 3-(4-chlorobutyl)-1H-indole-5-carbonitrile.

The processes for the preparation of 3-(4-chlorobutyl)-1H-indole-5-carbonitrile described in the aforementioned prior art suffer from disadvantages that the processes involve the use of highly dangerous, highly flammable and expensive reducing agents like diborane and bis(2-methoxyethoxy)aluminum hydride (Vitride/Red-Al), which are very difficult to handle at lab scale and commercial scale operations. Therefore, the use of these reducing agents is not advisable for scale up operations.

According to U.S. Pat. No. 6,509,475 B1 (hereinafter referred to as the '475 patent), it was not possible to isolate 3-(4-chlorobutyl)-1H-indole-5-carbonitrile when Lithium aluminium hydride (LiAlH$_4$) or Sodium borohydride with boron trifluoride etherate (NaBH$_4$/BF$_3$ ether) is used as a reducing agent for the reduction of 3-(4-chlorobutyryl)-1H-indole-5-carbonitrile.

U.S. Pat. No. 5,723,614 (hereinafter referred to as the '614 patent) discloses a process for the preparation of 5-(1-pipearzinyl)benzofuran-2-carboxamide. The synthesis is depicted in scheme 3:

Scheme 3:

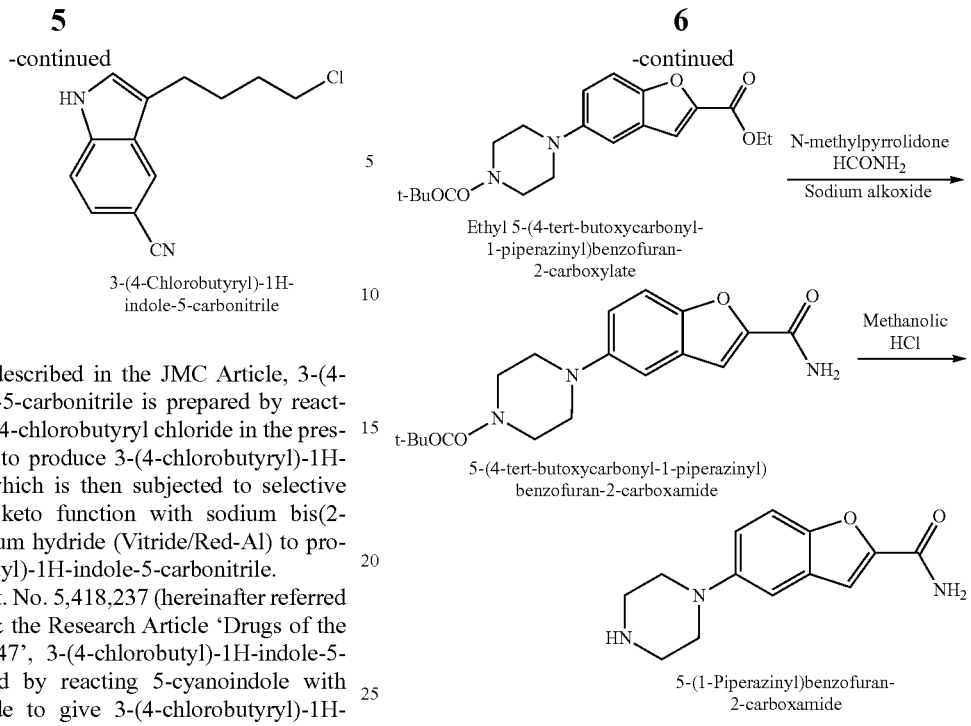

Ethyl 5-aminobenzofuran-
2-carboxylate

Ethyl 5-(1-piperazinyl)
benzofuran-2-carboxylate

Ethyl 5-(4-tert-butoxycarbonyl-
1-piperazinyl)benzofuran-
2-carboxylate 5-(4-tert-butoxycarbonyl-1-piperazinyl)
benzofuran-2-carboxamide 5-(1-Piperazinyl)benzofuran-
2-carboxamide According to the '614 patent, the preparation of 5-(1-pipearzinyl)benzofuran-2-carboxamide is carried out in four steps starting from ethyl 5-aminobenzofuran-2-carboxylate. According to first step, ethyl 5-(1-piperazinyl)benzofuran-2-carboxylate is prepared by reacting ethyl 5-aminobenzofuran-2-carboxylate with N,N-bis(2-chloroethyl)amine in dichloromethane to produce a reaction mass, followed by customary work-up using a solvent system (isopropanol/water 95:5). According to second step, the ethyl 5-(1-piperazinyl)benzofuran-2-carboxylate is subjected to BOC protection by reacting with di-tert-butyl dicarbonate in tetrahydrofuran to produce ethyl 5-(4-tert-butoxycarbonyl-1-piperazinyl)benzofuran-2-caboxylate. In third step, the ethyl 5-(4-tert-butoxycarbonyl-1-piperazinyl)benzofuran-2-caboxylate is reacted with formamide in the presence of sodium alkoxide in N-methylpyrrolidone to produce 5-(4-tert-butoxycarbonyl-1-piperazinyl)benzofuran-2-carboxamide. In fourth step, the 5-(4-tert-butoxycarbonyl-1-piperazinyl)benzofuran-2-carboxamide is then deprotected with methanolic HCl to produce the 5-(1-pipearzinyl)benzofuran-2-carboxamide.

Similar process for the preparation of ethyl 5-(1-piperazinyl)benzofuran-2-carboxylate is also reported in the JMC article. As per the process reported in the JMC article, the ethyl 5-(1-piperazinyl)benzofuran-2-carboxylate is prepared by heating a suspension of ethyl 5-aminobenzofuran-2-carboxylate, bis(2-chloroethyl)ammonium chloride and potassium carbonate to reflux temperature in 1-butanol for 48 hours. The hot suspension is decanted and filtered, followed by evaporation and subsequent re-crystallization of the crude product using methanol to produce the ethyl 5-(1-piperazinyl)benzofuran-2-carboxylate as a hydrochloride salt with 27% yield.

The processes for the preparation of vilazodone and its intermediates described in the aforementioned prior art suffer from disadvantages such as the use of additional and expensive reagents like 2-chloro-1-methylpyridinium methanesulfonate, 2-chloro-1-methylpyridinium iodide, di-tert-butyl dicarbonate, ethyldiisopropyl amine, formamide and sodium alkoxide; use of expensive and hazardous solvents like N-methylpyrrolidone, 1-butanol and tetrahydrofuran; use of tedious and cumbersome procedures like multiple process steps, prolonged reaction time periods, column chromatographic purifications, multiple isolations/re-crystallizations, and thus resulting in a poor product yield and quality. Methods involving column chromatographic purifications are generally undesirable for large-scale operations, thereby making the process commercially unfeasible.

CN 102267932 A (hereinafter referred to as CN'932 publication), describes a process for the preparation of vilazodone as depicted in scheme 4:

The present inventors have tried to reproduce the processes exemplified in the CN'932 publication. As a result, it has been found that most of the reactions described/exemplified in the CN'932 publication do not go to completion. For example, the reaction of 3-(4-chlorobutyryl)-1H-indole-5-carbonitrile with sodium borohydride in isopropanol as described in the CN'932 publication (Example 1 in page 8) does not end up with the formation of 3-(4-hydroxybutyl)-1H-indole-5-carbonitrile since this reaction is practically and theoretically impossible. Moreover, it has been observed by the present inventors that the condensation reaction

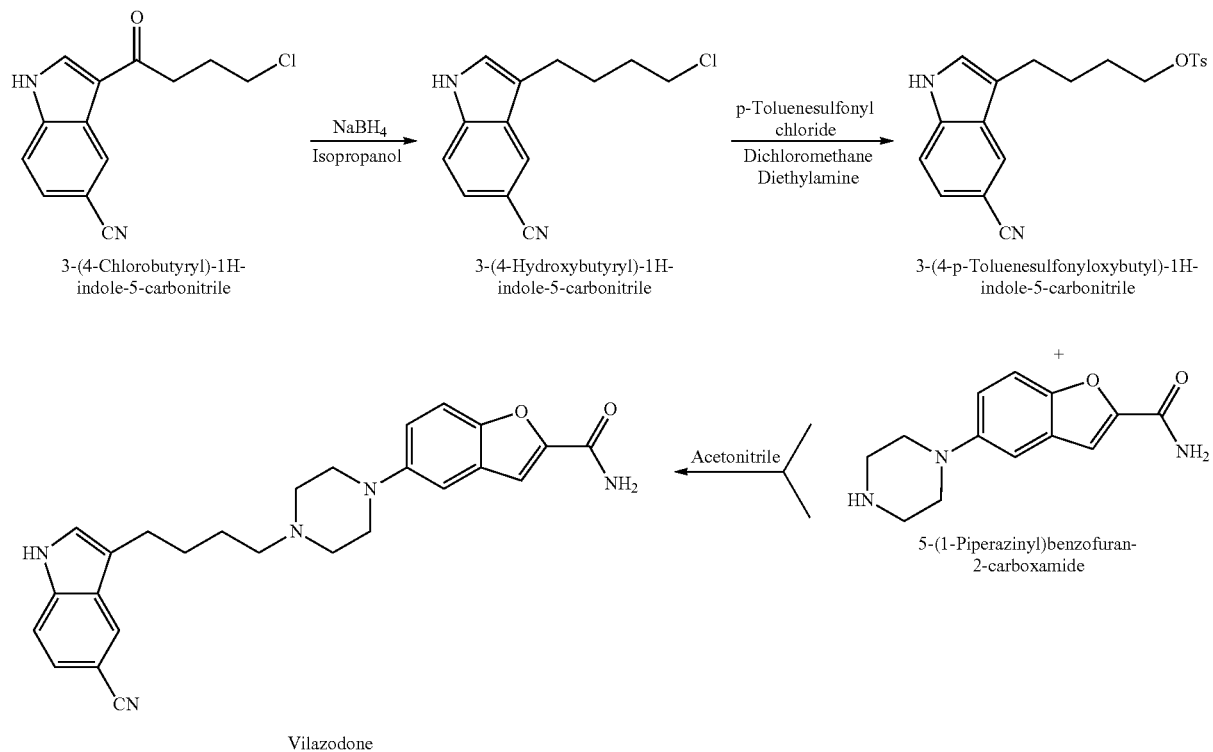

As per the process described in CN'932 publication, vilazodone is prepared by reacting 3-(4-chlorobutyryl)-1H-indole-5-carbonitrile with sodium borohydride in isopropanol at reflux temperature, followed by treating the reaction mass with dilute hydrochloric acid and subsequent workup and then subjecting to column chromatography purifications to produce 3-(4-hydroxybutyl)-1H-indole-5-carbonitrile. The hydroxylbutyl intermediate obtained is then subjected to sulfonylation using a sulfonylating agent selected from p-toluenesulfonyl chloride, benzenesulfonyl chloride, methanesulfonyl chloride and trifluoromethanesulfonyl chloride to produce corresponding sulfonylated intermediate, which is then condensed with 5-(1-piperazinyl)benzofuran-2-carboxamide in acetonitrile to produce vilazodone.

The processes for the preparation of vilazodone and its intermediates described in CN'932 publication suffer from several drawbacks since the processes are not reproducible and they involve expensive column chromatographic purifications, and the yields of vilazodone and its intermediates obtained are very low. Moreover, the vilazodone and its intermediates obtained by the processes described in the CN'932 publication do not have satisfactory purity.

between the 3-[4-(p-toluenesulfonyloxy)butyl]-1H-indole-5-carbonitrile and 5-(1-piperazinyl)benzofuran-2-carboxamide in acetonitrile exemplified in Example 6 of CN'932 publication does not go to completion even after maintenance of prolonged time periods.

U.S. Pat. No. 7,799,916 (hereinafter referred to as US'916 patent), describes two processes for the preparation of vilazodone as depicted in scheme 5:

Scheme 5:

Route-1:

5-Bromobenzofuran-2-carboxamide

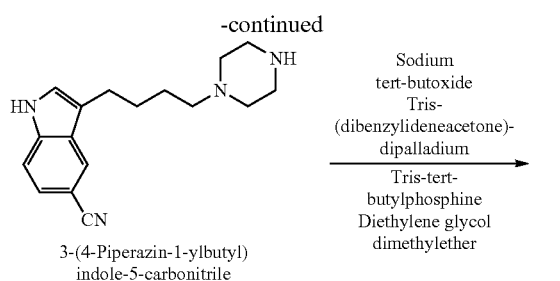

3-(4-Piperazin-1-ylbutyl)
indole-5-carbonitrile

Sodium
tert-butoxide
Tris-
(dibenzylideneacetone)-
dipalladium
⟶
Tris-tert-
butylphosphine
Diethylene glycol
dimethylether

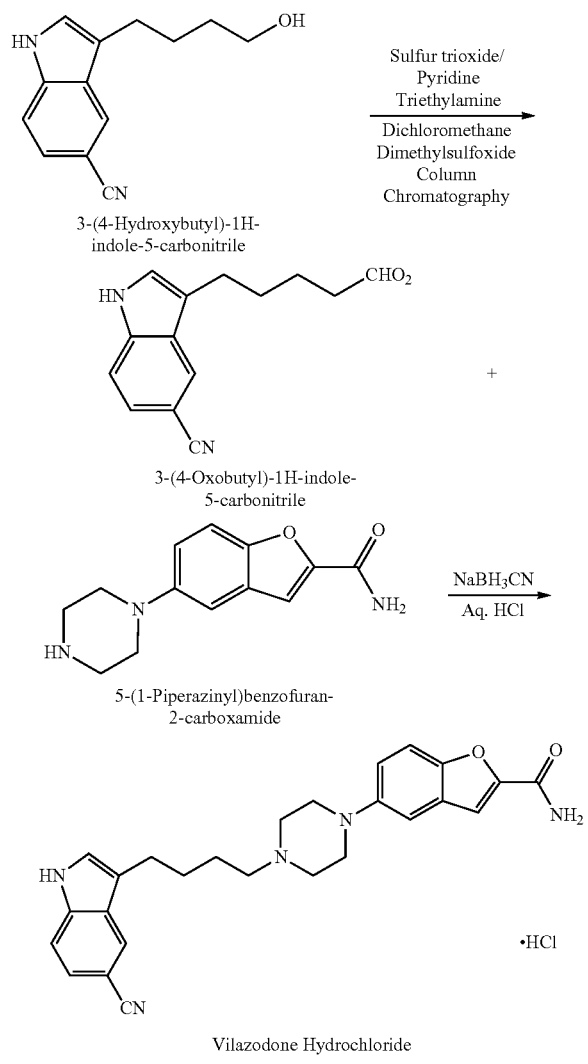

Vilazodone

Route-2:

3-(4-Hydroxybutyl)-1H-
indole-5-carbonitrile

Sulfur trioxide/
Pyridine
Triethylamine
⟶
Dichloromethane
Dimethylsulfoxide
Column
Chromatography 3-(4-Oxobutyl)-1H-indole-
5-carbonitrile

+

5-(1-Piperazinyl)benzofuran-
2-carboxamide

NaBH₃CN
⟶
Aq. HCl

Vilazodone Hydrochloride

According to first synthetic route described in US'916 patent, vilazodone is prepared by reacting 5-bromo-benzofuran-2-carboxamide with 3-(4-piperazin-1-ylbutyl)indole-5-carbonitrile in the presence of highly expensive reagents including tris(dibenzylidene acetone)dipalladium, tris-tert-butylphosphine, sodium tert-butoxide, and diethylene glycol dimethyl ether to produce a yellow-grey suspension, which is then heated at 120° C. for 48 hours, followed by cooling the reaction mass to room temperature and then subjecting the resulting mass to conventional working up to produce vilazodone fee base.

According to another synthetic process described in US '916 patent, vilazodone is prepared by reacting 3-(4-hydroxybutyl)-1H-indole-5-carbonitrile with sulfur trioxide/pyridine complex in dimethylsulfoxide to produce a reaction mass, followed by customary work up and then concentrating the resulting mass to produce an oily residue. The resulting residue is then chromatographed on silica gel using a mixture of dichloromethane and methyl tert-butyl ether to produce 3-(4-oxobutyl)-1H-indole-5-carbonitrile. The oxobutyl compound is reacted with 5-(1-piperazinyl)benzofuran-2-carboxamide in the presence of sodium cyanoborohydride to produce vilazodone free base, which is further treated with aqueous hydrochloric acid to produce vilazodone hydrochloride.

The processes for the preparation of vilazodone and its intermediates as described in the aforementioned prior art suffer from the following disadvantages and limitations:

a) the prior art processes involve the use of highly flammable and dangerous reagents like isobutyl-AlCl₂ (DIBAL), sodium bis(2-methoxyethoxy)aluminum hydride (Vitride/Red-Al), diborane, Lithium aluminium hydride (LiAlH₄) and boron trifluoride etherate (NaBH₄/BF₃ ether);

b) handling of the aforesaid reducing agents is very difficult at lab scale and in commercial scale operations;

c) the processes require longer reaction times and the yields and purity of the product obtained are very low;

d) the processes involve the use of highly hazardous and expensive reagents and solvents like 2-chloro-1-methyl-pyridinium methanesulfonate, 2-chloro-1-methylpyridinium iodide, N-methylpyrrolidone, di-tert-butyl dicarbonate, tris(dibenzylidene acetone)dipalladium, tris-tert-butylphosphine, diethylene glycol dimethyl ether, sulfur trioxide/pyridine complex and dimethylsulfoxide;

e) the processes involve the use of tedious and cumbersome procedures like prolonged reaction time periods, multiple process steps, column chromatographic purifications, multiple isolation/re-crystallizations;

f) methods involving column chromatographic purifications are generally undesirable for large-scale operations, thereby making the process commercially unfeasible;

g) the overall processes generate a large quantity of chemical waste which is difficult to treat.

Based on the aforementioned drawbacks, the prior art processes have been found to be unsuitable for the preparation of vilazodone and its intermediates at lab scale and in commercial scale operations.

A need remains for novel, commercially viable and environmentally friendly processes of preparing vilazodone and its intermediates with high yield and purity, to resolve the problems associated with the processes described in the prior art, and that will be suitable for large-scale preparation. Desirable process properties include non-hazardous conditions, environmentally friendly and easy to handle reagents, reduced process steps, reduced reaction time periods, reduced cost, greater simplicity, increased purity, and increased yield of the product, thereby enabling the production of vilazodone and its intermediates in high purity and with high yield.

SUMMARY OF THE INVENTION

The present inventors have surprisingly and unexpectedly found that benzofuran-2-carboxamide derivatives such as vilazodone and its intermediates can be prepared advantageously in high purity and with high yield, by amidating substituted or unsubstituted 5-(1-piperazinyl)benzofuran-2-carboxylic acid alkyl ester compound with ammonia in the presence of an alcohol solvent, preferably methanol. The novel process solves the drawbacks associated with the prior processes and is commercially viable for preparing benzofuran-2-carboxamide derivatives.

The present inventors have further surprisingly and unexpectedly found that 3-(4-hydroxybutyl)-1H-indole-5-carbonitrile intermediate can be prepared, in high purity and with high yield, by reacting 5-cyanoindole with 4-chlorobutyryl chloride in the presence of aluminium chloride to produce an intermediate compound, followed by reacting the compound with an aqueous alcohol to produce 3-(4-hydroxybutyryl)-1H-indole-5-carbonitrile, which is then reduced with sodium cyanoborohydride in the presence of hydrochloric acid and water in acetonitrile solvent to produce 3-(4-hydroxybutyl)-1H-indole-5-carbonitrile.

In one aspect, provided herein is efficient, industrially advantageous and environmentally friendly processes for the preparation of vilazodone and its key intermediates 5-(1-piperazinyl)benzofuran-2-carboxamide and 3-(4-hydroxybutyl)-1H-indole-5-carbonitrile, in high yield and with high purity, using reduced reaction steps, and without using additional and expensive reagents and expensive/hazardous solvents.

In another aspect, provided herein is an efficient, industrially advantageous and commercially viable process for the preparation of 5-(1-piperazinyl)benzofuran-2-carboxylic acid alkyl ester, in high yield and with high purity, using novel intermediates.

In another aspect, provided herein is a novel intermediate compound, 3-(4-hydroxybutyryl)-1H-indole-5-carbonitrile of formula VIII:

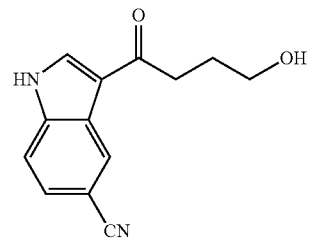

VIII or a salt thereof.

The processes for the preparation of vilazodone disclosed herein have the following advantages over the processes described in the prior art:
i) the processes involve the use of novel intermediate compound;
ii) the overall yield of the vilazodone product is increased and the purity of the product is increased without additional purifications such as multiple isolations and column chromatographic purifications;
iii) the processes avoid the use of highly inflammable, dangerous and difficult to handle reagents like DIBAL, sodium bis(2-methoxyethoxy)aluminum hydride, diborane, Lithium aluminium hydride and boron trifluoride etherate;
iv) the overall process involves shorter reactions times and less expensive reagents thereby making the process cost effective;
v) the processes avoid the use of additional and excess amounts of solvents, multiple isolation steps, column chromatographic purifications;
vi) the processes avoid the use of expensive and highly hazardous reagents like 2-chloro-1-methylpyridinium methanesulfonate, 2-chloro-1-methylpyridinium iodide, N-methylpyrrolidone, di-tert-butyl dicarbonate, tris (dibenzylidene acetone)dipalladium, tris-tert-butylphosphine, diethylene glycol dimethyl ether, sulfur trioxide/pyridine complex;
vii) the processes avoid the use of tedious and cumbersome procedures like prolonged reaction time periods, higher temperatures, column chromatographic purifications, multiple isolations, additional and excess amounts of solvents; and
viii) the processes involve easy work-up methods and simple isolation processes, and there is a reduction in chemical waste.

The processes for the preparation of Vilazodone using novel intermediate disclosed herein may be represented by a schematic diagram as depicted in scheme-6:

Schematic Representation:

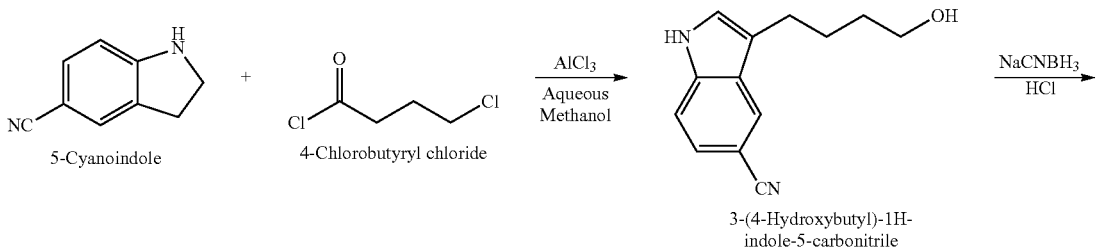

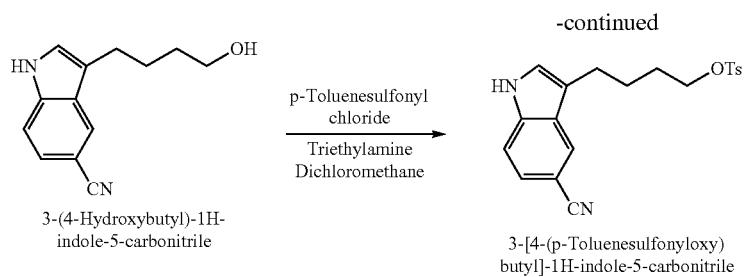
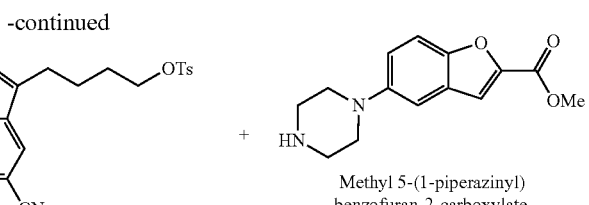
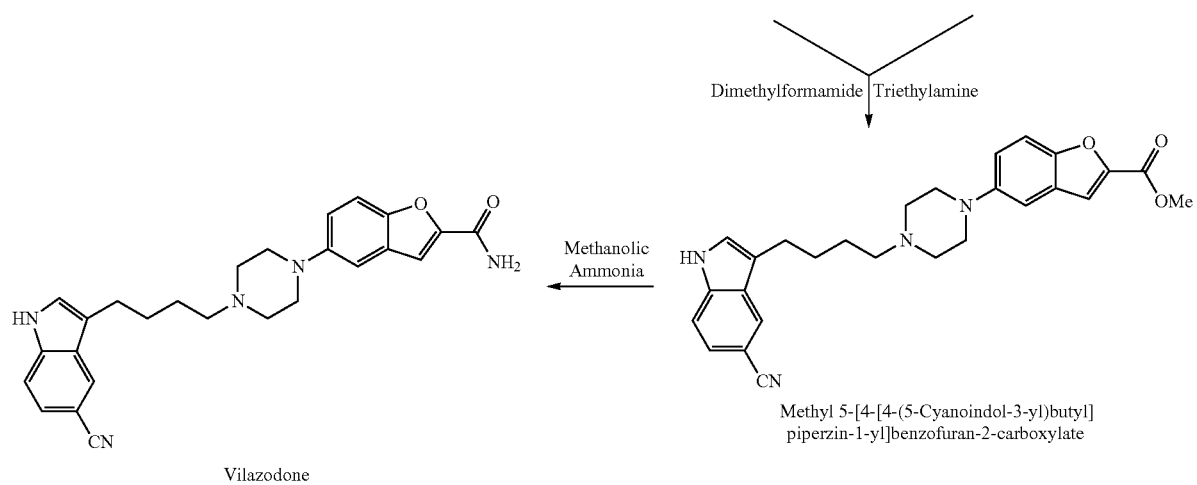

DETAILED DESCRIPTION OF THE INVENTION

According to one aspect, there is provided an improved process for the preparation of a benzofuran-2-carboxamide derivative of formula I:

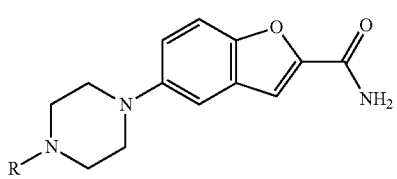

or a pharmaceutically acceptable salt thereof,
wherein R is H, a protecting group 'P', or an 'IND-Q-' radical,
wherein IND is an indol-3-yl radical, a 2,3-di-hydro-1H-indol-3-yl radical, or a 2-oxo-2,3-di-hydro-1H-indol-3-yl radical, which is unsubstituted or mono- or polysubstituted by OH, OA, CN, X, $COR_1$ or $CH_2R_1$;
Q is selected from $-(CH_2)_2-$, $-(CH_2)_3-$, and $-(CH_2)_4-$;
A is an alkyl group having 1 to 6 carbon atoms;
X is F, Cl, Br or I;
$R_1$ is OH, OA, $NH_2$, NHA or $NA_2$;
which comprises:
amidation of a benzofuran-2-carboxylic acid ester derivative of formula II:

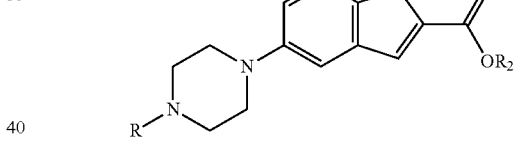

or a salt thereof, wherein R is as defined in formula I, and $R_2$ is an alkyl group having 1 to 4 carbon atoms;
with ammonia in a suitable solvent to produce the benzofuran-2-carboxamide compound of formula I, and optionally converting the compound of formula I obtained into a pharmaceutically acceptable salt thereof, wherein the ammonia is used in the form of aqueous ammonia or ammonia gas or ammonia saturated in an organic solvent.

In one embodiment, the compounds of formulae I and II wherein R is H.

In another embodiment, the compounds of formulae I and II wherein R is a nitrogen protecting group 'P'.

Exemplary nitrogen protecting groups 'P' include, but are not limited to, acetyl, pyrrolidinylmethyl, cumyl, benzhydryl, trityl, benzyloxycarbonyl (Cbz), 9-fluorenylmethyloxycarbonyl, benzyloxymethyl, pivaloyloxymethyl (POM), trichloroethxoycarbonyl, 1-adamantyloxycarbonyl, allyl, allyloxycarbonyl, trimethylsilyl, tert-butyldimethylsilyl, triethylsilyl, triisopropylsilyl, trimethylsilylethoxymethyl, t-butoxycarbonyl (BOC), t-butyl, 1-methyl-1,1-dimethylbenzyl and pivaloyl.

In another embodiment, the compounds of formulae I and II wherein R is an 'IND-Q-' radical.

Specifically, the radical IND is an indol-3-yl radical which is unsubstituted or mono- or disubstituted by the radicals indicated; and most specifically, it is substituted in the 5-position. Specific substituents on the indol-3-yl radical are selected from OH, OA, CN, CONH$_2$, CH$_2$OH, CO$_2$H, F, Cl, Br, I, CH$_2$NH$_2$, CONHA and CONA$_2$; and a most specific substituent is CN. Specifically, Q is —(CH$_2$)$_4$— group. The radical A is selected from methyl, ethyl, n-propyl, isopropyl, n-butyl, sec-butyl and tert-butyl; and specifically A is methyl or ethyl.

In a preferred embodiment, the compounds of formulae I and II wherein R is 4-(5-cyanoindol-3-yl)butyl radical.

Specifically, the group R$_2$ in the compounds of formula II is selected from methyl, ethyl, n-propyl, isopropyl, n-butyl, sec-butyl and tert-butyl; more specifically R$_2$ is methyl or ethyl; and most specifically R$_2$ is methyl.

In one embodiment, a specific benzofuran-2-carboxamide derivative of formula I prepared by the process described herein is 5-(1-pipearzinyl)benzofuran-2-carboxamide of formula I(i) (formula I, wherein R is H):

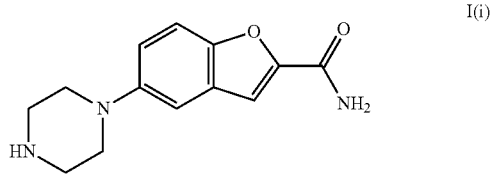

I(i)

or a salt thereof.

In another embodiment, a specific benzofuran-2-carboxamide derivative of formula I prepared by the process described herein is vilazodone of formula I(ii) (formula I, wherein R is 4-(5-cyanoindol-3-yl)butyl radical):

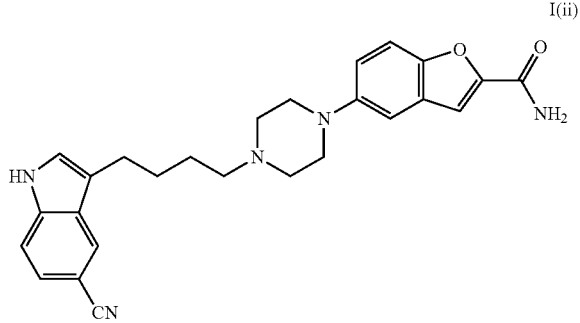 [SMILES: N#Cc1ccc2[nH]cc(CCCCN3CCN(c4ccc5oc(C(N)=O)cc5c4)CC3)c2c1]

I(ii)

or a pharmaceutically acceptable salt thereof.

Exemplary pharmaceutically acceptable salts of the benzofuran-2-carboxamide compound of formula I include, but are not limited to, hydrochloride, hydrobromide, sulfate, nitrate, phosphate, acetate, propionate, oxalate, succinate, maleate, fumarate, benzenesulfonate, toluenesulfonate, citrate, and tartrate. A specific pharmaceutically acceptable salt of the benzofuran-2-carboxamide compound of formula I is hydrochloride salt.

Exemplary acid addition salts of the ester compound of formula II include, but are not limited to, hydrochloride, hydrobromide, sulfate, nitrate, phosphate, acetate, propionate, oxalate, succinate, maleate, fumarate, benzenesulfonate, toluenesulfonate, citrate, and tartrate.

Exemplary solvents used in the amidation reaction include, but are not limited to water, an alcohol, and mixtures thereof.

Specifically, the solvent is selected from the group consisting of water, methanol, ethanol, n-propanol, isopropyl alcohol, isobutanol, n-butanol, tert-butanol, and mixtures thereof; more specifically the solvent is selected from the group consisting of water, methanol, ethanol, isopropyl alcohol, and mixtures thereof; and a most specific solvent is methanol.

In one embodiment, the organic solvent used for saturating ammonia gas is an alcohol solvent selected from the group as described above.

The reaction temperature and time period for amidation will ordinarily depend on the starting compound and the solvent employed in the reaction.

In one embodiment, the amidation reaction is carried out at a temperature of about 0° C. to about 50° C., specifically at a temperature of about 5° C. to about 45° C., and more specifically at a temperature of about 25° C. to about 35° C. The reaction time may vary from about 1 hour to about 25 hours, and more specifically from about 2 hours to about 10 hours.

In another embodiment, the amidation reaction is advantageously carried out using ammonia gas under pressure of about 1 Kg/Cm$^2$ to about 10 Kg/Cm$^2$, and specifically about 3 Kg/Cm$^2$ to about 5 Kg/Cm$^2$.

The reaction mass containing the benzofuran-2-carboxamide derivative of formula I obtained may be subjected to usual work up such as a washing, an extraction, an evaporation, a pH adjustment, a layer separation etc., followed by isolation and/or recrystallization from a suitable solvent by conventional methods such as cooling, seeding, partial removal of the solvent from the solution, by adding an anti-solvent to the solution, evaporation, vacuum distillation, or a combination thereof.

The solvent used for isolating/recrystallizing the pure benzofuran-2-carboxamide derivative of formula I is selected from the group consisting of water, acetone, methanol, ethanol, n-propanol, isopropanol, ethyl acetate, dichloromethane, toluene, N,N-dimethylformamide, dimethylsulfoxide, acetonitrile, and mixtures thereof.

The solid obtained is collected by filtration, filtration under vacuum, decantation, centrifugation, filtration employing a filtration media of a silica gel or celite, or a combination thereof.

The use of ammonia in the presence of a suitable solvent for the amidation reaction disclosed herein allows the product to be easily isolated and purified, thereby producing a product with high overall yield.

The benzofuran-2-carboxamide derivative of formula I, preferably vilazodone of formula I(ii), obtained by the process disclosed herein may be further dried in, for example, a Vacuum Tray Dryer, a Rotocon Vacuum Dryer, a Vacuum Paddle Dryer or a pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

In one embodiment, the drying is carried out at atmospheric pressure or reduced pressures, such as below about 200 mm Hg, or below about 50 mm Hg, at temperatures such as about 35° C. to about 90° C. The drying can be carried out for any desired time period that achieves the desired result, such as times about 1 to 20 hours. Drying may also be carried out for shorter or longer periods of time depending on the product specifications. Temperatures and pressures will be chosen based on the volatility of the solvent being used and the foregoing should be considered as only a general guidance. Drying can be suitably carried out in a tray dryer, vacuum oven, air oven, or using a fluidized bed drier, spin flash dryer, flash dryer, and the like.

The benzofuran-2-carboxamide derivative of formula I or a pharmaceutically acceptable salt thereof, preferably vilazodone of formula I(ii), obtained by the process disclosed herein has a purity of greater than about 98%, specifically greater than about 99%, more specifically greater than about 99.9%, and most specifically greater than about 99.95% as measured by HPLC.

According to another aspect, there is provided an improved process for preparing an alkyl 5-(1-piperazinyl)benzofuran-2-carboxylate compound of formula II(i):

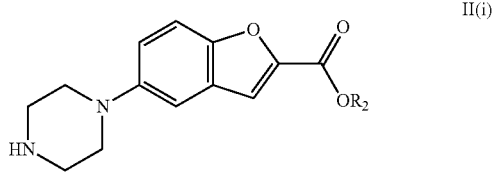

or an acid addition salt thereof, wherein $R_2$ is an alkyl group having 1 to 4 carbon atoms, comprising:

a) reacting an alkyl 5-aminobenzofuran-2-carboxylate compound of formula III:

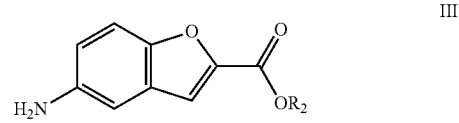

or an acid addition salt thereof, wherein $R_2$ is as defined in formula II(i);
with a sulfonamide compound of formula IV:

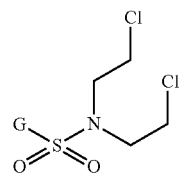

wherein G is selected from alkyl, cycloalkyl, and a phenyl radical which is unsubstituted or substituted by alkyl, alkoxy, halo, nitro, amino or acetyl amino group; in the presence of a base to produce a sulfonyl piperazine compound of formula V:

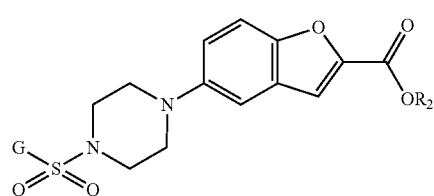

wherein G and $R_2$ are as defined above; and b) deprotecting the compound of formula V to produce the alkyl 5-(1-piperazinyl)benzofuran-2-carboxylate compound of formula II(i), and optionally converting the compound of formula II(i) obtained into an acid addition salt thereof.

Specifically, the group '$R_2$' in the compounds of formulae II(i), III and V is selected from methyl, ethyl, n-propyl, isopropyl, n-butyl, sec-butyl and tert-butyl; more specifically $R_2$ is methyl or ethyl; and most specifically $R_2$ is methyl.

Except otherwise stated, the term "alkyl" denotes an aliphatic hydrocarbon group which may be straight or branched having 1 to 10 carbon atoms in the chain, preferably 1 to 6 carbon atoms in the chain; the term "cycloalkyl" denotes a non-aromatic ring system of 3 to 6 carbon atoms, preferably of 6 carbon atoms; and the term "alkoxy" refers to an alkoxy group having 1 to 5 carbon atoms, preferably methoxy group. Exemplary alkyl groups include methyl, ethyl, n-propyl, iso-propyl, n-butyl, iso-butyl, t-butyl and n-pentyl. Exemplary cycloalkyl groups include cyclopentyl, cyclohexyl, and the like.

Specifically, the group 'G' in the compounds of formulae IV and V is selected from methyl, ethyl, cyclohexyl, phenyl, tolyl, methoxy substituted phenyl, chloro substituted phenyl and nitro substituted phenyl; more specifically G is methyl, phenyl or p-tolyl; and most specifically G is phenyl.

Unless otherwise specified, the term 'salt' as used herein may include acid addition salts and base addition salts.

Acid addition salts, as used herein, include the salts that are derived from organic and inorganic acids. For example, the acid addition salts are derived from a therapeutically acceptable acid such as hydrochloric acid, hydrobromic acid, sulfuric acid, nitric acid, oxalic acid, acetic acid, propionic acid, phosphoric acid, succinic acid, maleic acid, fumaric acid, citric acid, glutaric acid, tartaric acid, benzenesulfonic acid, toluenesulfonic acid, di-p-toluoyl-L-(+)-tartaric acid, malic acid, ascorbic acid, and the like.

Base addition salts may be derived from an organic or an inorganic base. For example, the base addition salts are derived from alkali or alkaline earth metals such as sodium, calcium, potassium and magnesium; ammonium salt, organic amines such as ethylamine, tert-butylamine, diethylamine, diisopropylamine, and the like.

In one embodiment, the reaction in step-(a) is carried out at a temperature of about 20° C. to about 100° C. for about 1 hour to about 50 hours, specifically at a temperature of about 50° C. to about 90° C. for about 5 hours to about 48 hours, and more specifically at about 70° C. to about 80° C. for about 15 hours to about 45 hours.

The reaction in step-(a) may be carried out in the presence or absence of a reaction inert solvent. In one embodiment, the base in step-(a) is used as both solvent and acid scavenger.

However, it is also possible to carry out the reaction in step-(a) in the presence of a reaction inert solvent. Exemplary inert solvents may include, but are not limited to, water, an alcohol, a ketone, a chlorinated hydrocarbon solvent, an ester, an ether, a polar aprotic solvent, and mixtures thereof. For example, the inert solvent may be selected from the group consisting of water, methanol, ethanol, n-propanol, isopropyl alcohol, isobutanol, n-butanol, tert-butanol, acetone, methyl ethyl ketone, methyl isobutyl ketone, methyl tert-butyl ketone, methylene chloride, ethylene dichloride, ethyl acetate, methyl acetate, isopropyl acetate, tert-butyl methyl acetate, ethyl formate, tetrahydrofuran, 2-methyl tetrahydrofuran, dioxane, diethyl ether, diisopropyl ether, methyl tert-butyl ether, monoglyme, diglyme, N,N-dimethylformamide, N,N-dimethylacetamide, dimethylsulfoxide, and mixtures thereof.

The base used in step-(a) is an organic or inorganic base, and specifically an organic base.

Exemplary organic bases include, but are not limited to, trimethylamine, tributylamine, triethylamine, dibutylamine, diisopropylethylamine, N-methylmorpholine, N-ethylmorpholine, 4-(N,N-dimethylamino)pyridine, N,N-dimethylaniline and 1-alkylimidazole.

Exemplary inorganic bases include, but are not limited to, hydroxides, alkoxides, bicarbonates and carbonates of alkali or alkaline earth metals. Specific inorganic bases are sodium hydroxide, calcium hydroxide, magnesium hydroxide, potassium hydroxide, lithium hydroxide, sodium carbonate, potassium carbonate, sodium bicarbonate, potassium bicarbonate, lithium carbonate, sodium tert-butoxide, sodium isopropoxide and potassium tert-butoxide.

Specifically, the base used in step-(a) is tributylamine or triethylamine, and most specifically tributylamine.

In one embodiment, the base in step-(a) is used in a ratio of about 1 to 20 equivalents, specifically about 5 to 10 equivalents, with respect to the compound of formula III in order to ensure a proper course of the reaction.

The reaction mass containing the sulfonyl piperazine compound of formula V obtained in step-(a) may be subjected to usual work up such as a washing, an extraction, a pH adjustment, an evaporation, a layer separation or a combination thereof. The reaction mass may be used directly in the next step to produce the compound of formula II(i), or the compound of formula V may be isolated and then used in the next step.

In one embodiment, the sulfonyl piperazine compound of formula V is isolated from a suitable solvent by conventional methods such as cooling, seeding, partial removal of the solvent from the solution, by adding an anti-solvent to the solution, evaporation, vacuum distillation, or a combination thereof.

The solvent used to isolate the compound of formula V is selected from the group consisting of water, an alcohol, an ether, an ester, a hydrocarbon solvent, a chlorinated hydrocarbon, and mixtures thereof. Specifically, the solvent is selected from the group consisting of water, methanol, ethanol, iso-propanol, tetrahydrofuran, 1,4-dioxane, 2-methyl-tetrahydrofuran, diisopropyl ether, methyl tert-butyl ether, ethyl acetate, n-pentane, n-hexane, n-heptane, cyclohexane, toluene, xylene, dichloromethane, dichloroethane, chloroform, and mixtures thereof. A most specific solvent is methanol.

In a specific embodiment, the isolation of the compound of formula V is carried out by cooling the reaction mass, followed by the addition of methanol at a temperature of about 25° C. to about 35° C., and more specifically at a temperature of about 25° C. to about 30° C. After completion of addition process, the resulting mass is stirred at a temperature of about 25° C. to about 35° C. for at least 10 minutes, and most specifically at a temperature of about 25° C. to about 30° C. for about 15 minutes to about 2 hours.

In one embodiment, the deprotection reaction in step-(b) is carried out in the presence of an acid. The acid can be an organic acid or an inorganic acid or a combination thereof.

Specifically, the acid is selected from the group consisting of the hydrochloric acid, hydrobromic acid, sulfuric acid, nitric acid, oxalic acid, acetic acid, propionic acid, phosphoric acid, 4-hydroxybenzoic acid, or a combination thereof; more specifically the acid is hydrochloric acid, hydrobromic acid, sulfuric acid, acetic acid, 4-hydroxybenzoic acid, or a combination thereof; and a most specific acid is sulfuric acid or hydrobromic acid in acetic acid.

The deprotection reaction in step-(b) may be carried out in the presence or absence of a reaction inert solvent. In one embodiment, the acid employed for deprotection is also used as solvent. The reaction inert solvent may be selected from the group as described above.

In one embodiment, the deprotection reaction in step-(b) is carried out at a temperature of about 20° C. to about 120° C. for at least 5 minutes, specifically at a temperature of about 80° C. to about 110° C. for about 10 minutes to about 2 hours, and more specifically at about 95° C. to about 105° C. for about 15 minutes to about 1 hour.

In one embodiment, the acid in step-(b) is used in a ratio of about 0.5 to 10 equivalents, specifically about 1 to 2.5 equivalents, with respect to the compound of formula V in order to ensure a proper course of the reaction.

The reaction mass containing the alkyl 5-(1-piperazinyl)benzofuran-2-carboxylate compound of formula II(i) obtained in step-(b) may be subjected to usual work up such as a washing, an extraction, an evaporation, a pH adjustment, a layer separation etc., followed by isolation from a suitable solvent by the methods as described hereinabove.

In a specific embodiment, the reaction mass containing the alkyl 5-(1-piperazinyl)benzofuran-2-carboxylate compound of formula II(i) obtained in step-(b) is quenched with ice cold water, followed by adjusting the pH of the aqueous layer to a basic value and then extracting with ethyl acetate and subsequent removal of the solvent by distillation to produce pure alkyl 5-(1-piperazinyl)benzofuran-2-carboxylate compound of formula II(i).

The solid obtained in any of the above process steps may be collected by filtration, filtration under vacuum, decantation, centrifugation, filtration employing a filtration media of a silica gel or celite, or a combination thereof.

In one embodiment, a specific compound of formula II(i) prepared by the process described herein is methyl 5-(1-piperazinyl)benzofuran-2-carboxylate of formula II(i)(a) (formula II(i), wherein $R_2$ is methyl):

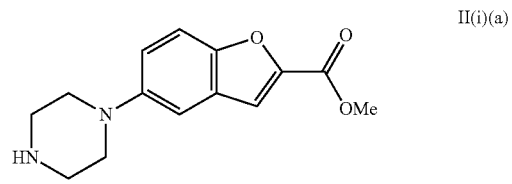 [SMILES: COC(=O)c1cc2cc(N3CCNCC3)ccc2o1]

II(i)(a)

or an acid addition salt thereof.

The use of inexpensive, non-hazardous, readily available and easy to handle reagents allows the processes disclosed herein to be suitable for the preparation of vilazodone and its intermediates at lab scale and in commercial scale operations.

Exemplary acid addition salts of the ester compound of formula II(i) and III include, but are not limited to, hydrochloride, hydrobromide, sulfate, nitrate, phosphate, acetate, propionate, oxalate, succinate, maleate, fumarate, benzenesulfonate, toluenesulfonate, citrate, and tartrate.

According to another aspect, there is provided an improved and cost effective process for the preparation of vilazodone of formula I(ii):

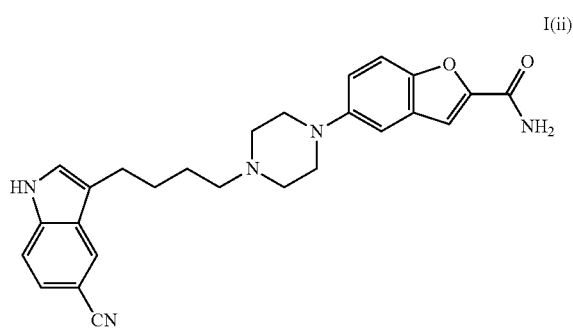 [SMILES: N#Cc1ccc2[nH]cc(CCCCN3CCN(c4ccc5oc(C(N)=O)cc5c4)CC3)c2c1]

or a pharmaceutically acceptable salt thereof, which comprises:

a) reacting 5-cyanoindole of formula IX:

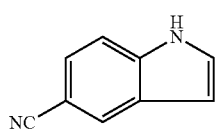

with 4-chlorobutyryl chloride of formula X:

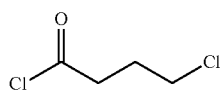

in the presence of a Lewis acid in a suitable solvent to produce a reaction mass;

b) isolating the compound from the reaction mass obtained in step-(a);

c) reacting the compound obtained in step-(b) with an alcohol or an aqueous alcohol to produce 3-(4-hydroxybutyryl)-1H-indole-5-carbonitrile of formula VIII:

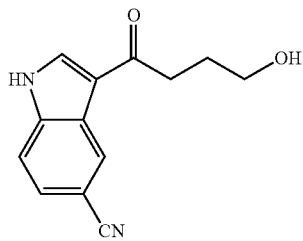

or a salt thereof;

d) reducing the hydroxybutyryl compound of formula VIII with a suitable reducing agent in the presence of an acid to produce 3-(4-hydroxybutyl)-1H-indole-5-carbonitrile of formula VII:

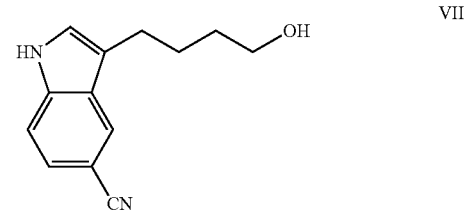 [SMILES: N#Cc1ccc2[nH]cc(CCCCO)c2c1]

or a salt thereof;

e) converting the hydroxybutyl compound of formula VII obtained in step-(d) into its sulfonyl ester derivative of formula VI:

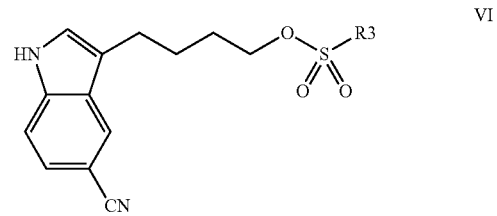

or a salt thereof, wherein $R_3$ is an alkyl, cycloalkyl, haloalkyl, aralkyl, or a substituted or unsubstituted aryl group;

f) reacting the sulfonyl compound of formula VI with an alkyl 5-(1-piperazinyl)benzofuran-2-carboxylate compound of formula II(i):

II(i)

or an acid addition salt thereof, wherein $R_2$ is an alkyl group having 1 to 4 carbon atoms, in the presence of a base in a suitable solvent to produce an alkyl 5-[4-[4-(5-cyanoindol-3-yl)butyl]piperazin-1-yl]benzofuran-2-carboxylate of formula II(ii):

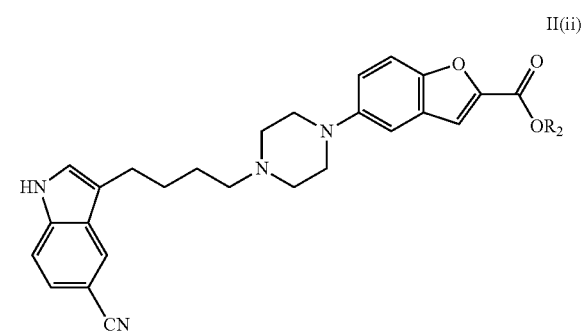

or an acid addition salt thereof; and g) amidation of the carboxylate compound of formula II(ii) or an acid addition salt thereof to produce the vilazodone of formula I(ii), and optionally converting the vilazodone obtained into a pharmaceutically acceptable salt thereof.

Unless otherwise specified, the term "alkyl", as used herein, denotes an aliphatic hydrocarbon group which may be straight or branched having 1 to 12 carbon atoms in the chain. Preferred alkyl groups have 1 to 4 carbon atoms in the chain. The alkyl may be substituted with one or more "cycloalkyl groups". Exemplary alkyl groups include methyl, ethyl, n-propyl, iso-propyl, n-butyl, iso-butyl, t-butyl, and n-pentyl.

The term "cycloalkyl", as used herein, denotes a non-aromatic mono- or multicyclic ring system of 3 to 10 carbon atoms, preferably of about 5 to about 10 carbon atoms. Exemplary monocyclic cycloalkyl groups include cyclopentyl, cyclohexyl, cycloheptyl and the like.

The term "aryl", as used herein, denotes an aromatic monocyclic or multicyclic ring system of 6 to 10 carbon atoms. The aryl is optionally substituted with one or more "ring system substituents" which may be the same or different, and are as defined herein. Exemplary aryl groups include phenyl, tolyl or naphthyl.

The term "aralkyl", as used herein, denotes an aryl-alkyl group wherein the aryl and alkyl are as herein described. Preferred aralkyls contain a lower alkyl moiety. Exemplary aralkyl groups include benzyl, 2-phenethyl and naphthalenemethyl.

Specifically, the group '$R_2$' in the compounds of formulae II(i) and II(ii) is selected from methyl, ethyl, n-propyl, isopropyl, n-butyl, sec-butyl and tert-butyl; more specifically $R_2$ is methyl or ethyl; and most specifically $R_2$ is methyl.

Specifically, the group 'R3' in the compound of formula VI is selected from the group consisting of methyl, ethyl, propyl, isopropyl, isobutyl, chloromethyl, fluoromethyl, trifluoromethyl, phenyl, p-tolyl, benzyl, 4-nitrophenyl, 4-chlorophenyl, 3-nitrophenyl, 4-chlorobenzyl, and the like; and most specifically, 'R3' is methyl, benzyl, p-tolyl or trifluoromethyl.

The 3-(4-hydroxybutyryl)-1H-indole-5-carbonitrile of formula VIII disclosed herein is novel and constitute another aspect of the present invention.

The use of the 3-(4-hydroxybutyryl)-1H-indole-5-carbonitrile of formula VIII in the preparation of vilazodone of formula I(ii) or a pharmaceutical acceptable salt thereof is novel and forms further aspect of the present invention.

Advantageously, the novel intermediate compound of vilazodone disclosed herein is obtained as a solid state form in substantially pure form.

The term "substantially pure" as used herein refers to the hydroxybutyryl compound, disclosed herein, having a purity of greater than about 90 wt %, specifically greater than about 95 wt %, more specifically greater than about 98 wt %, and still more specifically greater than about 99 wt %. The purity is preferably measured by High Performance Liquid Chromatography (HPLC). For example, the purity of the hydroxybutyryl compound obtained by the processes disclosed herein can be about 95% to about 99%, or about 98% to about 99.9%, as measured by HPLC.

Exemplary Lewis acids used in step-(a) include, but are not limited to, aluminium chloride, calcium chloride, zinc chloride, ferric chloride, and the like. A most specific Lewis acid is aluminium chloride.

In one embodiment, the solvent used in step-(a) is a halogenated hydrocarbon solvent. Specifically, the halogenated hydrocarbon solvent is selected from the group consisting of dichloromethane, dichloroethane, chloroform, carbon tetrachloride, and mixtures thereof; and a most specific halogenated hydrocarbon solvent is dichloromethane.

The reaction temperature and time period will ordinarily depend on the starting compounds and the solvent/reagent employed in the reaction.

In one embodiment, the reaction in step-(a) is carried out at a temperature of about −10° C. to the reflux temperature of the solvent used, specifically at a temperature of about −5° C. to about 50° C., and more specifically at about 0° C. to about 35° C. The reaction time may vary between about 1 hour to about 20 hours, specifically about 4 hours to about 18 hours, and more specifically about 8 hours to about 16 hours.

The reaction mass obtained in step-(a) may be subjected to usual work up such as a washing, an extraction, a pH adjustment, an evaporation, a layer separation, a decolorization, or a combination thereof.

In one embodiment, the isolation in step-(b) is carried out by cooling, seeding, partial removal of the solvent from the solution, by adding an anti-solvent to the solution, evaporation, vacuum distillation, or a combination thereof.

In another embodiment, the isolation in step-(b) is carried out by pouring the reaction mass into crushed ice with slow stirring and the resulting mixture is stirred at a temperature of about −5° C. to about 10° C. for about 20 minutes to about 2 hours, and most specifically at a temperature of about 0° C. to about 5° C. for about 1 hour.

The solid obtained in step-(b) is collected by filtration, filtration under vacuum, decantation, centrifugation, filtration employing a filtration media of a silica gel or celite, or a combination thereof.

Exemplary alcohols used in step-(c) include, but are not limited to, methanol, ethanol, isopropanol, n-butanol, and mixtures thereof. A most specific alcohol is methanol.

The term "aqueous alcohol" as used herein refers to a solution or medium comprising water and an alcohol. Specifically, the ratio of water to the alcohol in the aqueous alcohol solution employed in step-(c) is from about 1:10 to about 10:1 (volume/volume), and most specifically about 1:1 (volume/volume). A most specific aqueous alcohol is aqueous methanol.

In one embodiment, the amount of the alcohol or aqueous alcohol employed in step-(c) is about 5 volumes to about 30 volumes, and more specifically about 15 volumes to about 25 volumes, per gram of the compound obtained in step-(b).

In one embodiment, the reaction in step-(c) is carried out by heating the contents under stirring at a temperature of about 40° C. to the reflux temperature of the alcohol or aqueous alcohol solution used, and most specifically at the reflux temperature of the alcohol or aqueous alcohol solution used. The reaction time may vary between about 30 minutes to about 5 hours, specifically about 1 hour to about 4 hours, and more specifically about 2 hours to about 4 hours.

The reaction mass containing the 3-(4-hydroxybutyryl)-1H-indole-5-carbonitrile of formula VIII or a salt thereof obtained in step-(c) may be subjected to usual work up such as washing, carbon treatment, an extraction, a pH adjustment, an evaporation, a layer separation, decolorization, or a combination thereof. The reaction mass may be used directly in the next step to produce the 3-(4-hydroxybutyl)-1H-indole-5-carbonitrile of formula VII or a salt thereof, or the compound of formula VIII may be isolated and/or recrystallized and then used in the next step.

In one embodiment, the hydroxybutyryl compound of formula VIII is isolated from a suitable solvent by conventional methods such as cooling, seeding, partial removal of the solvent from the solution, by adding an anti-solvent to the solution, evaporation, vacuum distillation, or a combination thereof.

The solvent used for isolating the hydroxybutyryl compound of formula VIII is an aqueous alcohol solvent as described hereinabove.

Exemplary reducing agents used in step-(d) include, but are not limited to, metal hydrides such as sodium borohydride, sodium cyanoborohydride, and the like. Specifically, the reducing agent used in step-(d) is sodium cyanoborohydride.

Exemplary acids used in step-(d) include, but are not limited to, organic acids, inorganic acid, Lewis acids, and mixtures thereof.

In one embodiment, the acid used in step-(d) is selected from the group consisting of hydrochloric acid, hydrobromic acid, sulfuric acid, nitric acid, oxalic acid, acetic acid, propionic acid, phosphoric acid, succinic acid, maleic acid, fumaric acid, citric acid, glutaric acid, tartaric acid, benzenesulfonic acid, toluenesulfonic acid, malic acid, ascorbic acid, and the like. Specifically, the acid is hydrochloric acid or hydrobromic acid, and a most specific acid is hydrochloric acid.

For example, hydrochloric acid used may be in the form of concentrated hydrochloric acid, aqueous hydrochloric acid or in the form of hydrogen chloride dissolved in an organic solvent. The organic solvent used for dissolving hydrogen chloride gas or hydrogen chloride is selected from the group consisting of ethanol, methanol, isopropyl alcohol, ethyl acetate, diethyl ether, dimethyl ether and acetone.

In one embodiment, the reduction in step-(d) is carried out in the presence of a reaction inert solvent. The term solvent also includes mixture of solvents.

Exemplary reaction inert solvents used in step-(d) include, but are not limited to, a hydrocarbon solvent, an ether, a nitrile, a halogenated hydrocarbon solvent, and mixtures thereof.

Specifically, the solvent used in step-(d) is selected from the group consisting of n-pentane, n-hexane, n-heptane, cyclohexane, toluene, xylene, tetrahydrofuran, 2-methyltetrahydrofuran, dioxane, diethyl ether, diisopropyl ether, methyl tert-butyl ether, monoglyme, diglyme, acetonitrile, propionitrile, dichloromethane, dichloroethane, and mixtures thereof. A most specific solvent is acetonitrile.

In one embodiment, the reduction in step-(d) is carried out at a temperature of about −10° C. to the reflux temperature of the solvent used, specifically at a temperature of about 0° C. to about 40° C., and more specifically at about 0° C. to about 10° C. The reaction time may vary between about 10 minutes to about 5 hours, and most specifically about 10 minutes to about 2 hours.

The reaction mass containing the 3-(4-hydroxybutyl)-1H-indole-5-carbonitrile of formula VII obtained in step-(d) may be subjected to usual work up such as washing, carbon treatment, an extraction, a pH adjustment, an evaporation, a layer separation, decolorization, or a combination thereof. The reaction mass may be used directly in the next step to produce the sulfonyl compound of formula VI, or the hydroxybutyl compound of formula VII may be isolated and/or recrystallized and then used in the next step.

In one embodiment, the hydroxybutyl compound of formula VII is isolated and/or re-crystallized from a suitable solvent by conventional methods such as cooling, seeding, partial removal of the solvent from the solution, by adding an anti-solvent to the solution, evaporation, vacuum distillation, or a combination thereof.

The solvent used for isolating and/or recrystallizing the hydroxybutyl compound of formula VII is selected from the group consisting of dichloromethane, dichloroethane, chloroform, and mixtures thereof.

The conversion of the hydroxybutyl compound of formula VII into its sulfonyl ester derivative of formula VI in step-(e) can be carried out by the methods described in the prior art, for example, the processes described in the Chinese Patent Application Publication No. CN 102267932 A.

The reaction in step-(f) is carried out in the presence of a suitable reaction inert solvent. Exemplary solvents used in step-(f) include, but are not limited to, a polar aprotic solvent, an alcohol, and mixtures thereof.

Specifically, the solvent used in step-(f) is selected from the group consisting of N,N-dimethylformamide, N,N-dimethylacetamide, dimethylsulfoxide, methanol, ethanol, isopropanol, and mixtures thereof. A most specific solvent is N,N-dimethylformamide or N,N-dimethylacetamide.

It has been surprisingly and unexpectedly found that the yield of the alkyl 5-[4-[4-(5-cyanoindol-3-yl)butyl]piperazin-1-yl]benzofuran-2-carboxylate of formula II(ii) obtained in step-(f) is significantly increased when polar aprotic solvent (preferably N,N-dimethylformamide) is used as a solvent. The present inventors have further observed that when acetonitrile is used as a solvent in step-(f) the reaction does not go to completion even after maintenance of prolonged time periods.

The base used in step-(f) is an organic or inorganic base selected from the group as described hereinabove. Specifically, the base is an organic base and most specifically triethylamine.

In one embodiment, the reaction in step-(f) is carried out at a temperature of about 0° C. to about the reflux temperature of the solvent used, specifically at a temperature of about 50° C. to about 90° C., and more specifically at a temperature of about 75° C. to about 85° C. The reaction time may vary from about 20 minutes to about 4 hours, specifically from about 30 minutes to about 2 hours, and more specifically from about 40 minutes to about 1 hour.

The reaction mass containing the alkyl 5-[4-[4-(5-cyanoindol-3-yl)butyl]piperazin-1-yl]benzofuran-2-carboxylate of formula II(ii) obtained in step-(f) may be subjected to usual work up methods as described hereinabove. The reaction mass may be used directly in the next step to produce the vilazodone of formula I(ii), or the carboxylate compound of formula II(ii) may be isolated and/or recrystallized and then used in the next step. After completion of the reaction, water was added to the reaction mass at a temperature of about 20° C. to about 30° C., followed by stirring at the same temperature.

In one embodiment, the carboxylate compound of formula II(ii) is isolated and/or re-crystallized from a suitable solvent by conventional methods as described hereinabove.

The solvent used for isolating and/or recrystallizing the carboxylate compound of formula II(ii) is selected from the group consisting of water, an alcohol, a ketone, an ether, an ester, a hydrocarbon solvent, a halogenated hydrocarbon, and mixtures thereof.

In one embodiment, a most specific alkyl 5-[4-[4-(5-cyanoindol-3-yl)butyl]piperazin-1-yl]benzofuran-2-carboxylate of formula II(ii) prepared by the process described herein is methyl 5-[4-[4-(5-cyanoindol-3-yl)butyl]piperazin-1-yl]benzofuran-2-carboxylate of formula II(ii)(a) (formula II(ii), wherein $R_2$ is methyl):

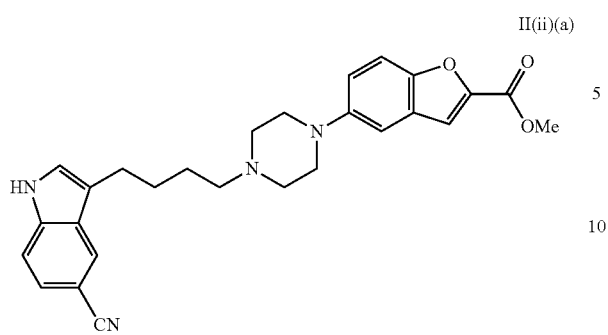

II(ii)(a)

or a salt thereof.

In one embodiment, the amidation reaction in step-(g) is advantageously carried out using ammonia in a suitable solvent by the methods as described hereinabove. Specifically, the amidation reaction in step-(g) is carried out using ammonia in a solvent selected from the group consisting of water, methanol, ethanol, isopropyl alcohol, and mixtures thereof.

In another embodiment, the highly pure vilazodone of formula I(ii) obtained in step-(g) is isolated and/or recrystallized and then collected by the methods as described hereinabove.

Pharmaceutically acceptable salts of vilazodone, preferably vilazodone hydrochloride, can be prepared in high purity by using the highly pure vilazodone, obtained by the processes disclosed herein, by known methods.

The vilazodone of formula I(ii) or a pharmaceutically acceptable salt thereof obtained by the process disclosed herein has a purity of greater than about 98%, specifically greater than about 99%, more specifically greater than about 99.9%, and most specifically greater than about 99.95% as measured by HPLC.

According to another aspect, there is provided a novel intermediate compound, 3-(4-hydroxybutyryl)-1H-indole-5-carbonitrile of formula VIII:

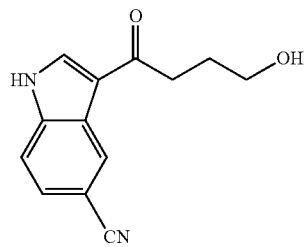

VIII or a salt thereof.

According to another aspect, there is provided a process for the preparation of 3-(4-hydroxybutyryl)-1H-indole-5-carbonitrile of formula VIII:

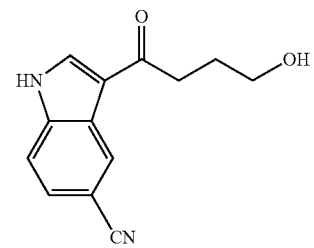

VIII or a salt thereof, comprising:
a) reacting 5-cyanoindole of formula IX:

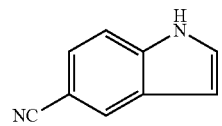

IX with 4-chlorobutyryl chloride of formula X:

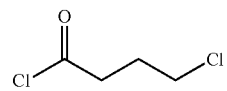

X in the presence of a Lewis acid in a suitable solvent to produce a reaction mass;
b) isolating the compound from the reaction mass obtained in step-(a); and
c) reacting the compound obtained in step-(b) with an alcohol or an aqueous alcohol to produce 3-(4-hydroxybutyryl)-1H-indole-5-carbonitrile of formula VIII or a salt thereof.

The above process steps (a, b & c) for the preparation of 3-(4-hydroxybutyryl)-1H-indole-5-carbonitrile of formula VIII are carried out by using the methods, reagents and parameters as described hereinabove.

According to another aspect, there is provided a process for the preparation of 3-(4-hydroxybutyl)-1H-indole-5-carbonitrile of formula VII:

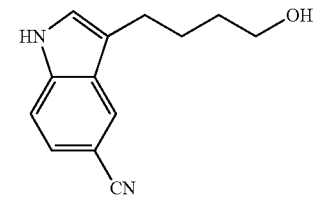

VII or a salt thereof, comprising:
a) reacting 5-cyanoindole of formula IX:

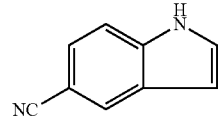

IX with 4-chlorobutyryl chloride of formula X:

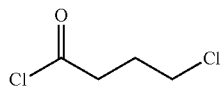

in the presence of a Lewis acid in a suitable solvent to produce a reaction mass;
b) isolating the compound from the reaction mass obtained in step-(a);
c) reacting the compound obtained in step-(b) with an alcohol or an aqueous alcohol to produce 3-(4-hydroxybutyryl)-1H-indole-5-carbonitrile of formula VIII:

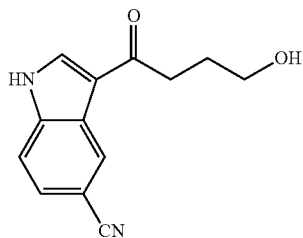

or a salt thereof; and
d) reducing the hydroxybutyryl compound of formula VIII with a suitable reducing agent in the presence of an acid to produce 3-(4-hydroxybutyl)-1H-indole-5-carbonitrile of formula VII or a salt thereof.

The above process steps (a, b, c & d) for the preparation of 3-(4-hydroxybutyl)-1H-indole-5-carbonitrile of formula VII are carried out by using the methods, reagents and parameters as described hereinabove.

According to another aspect, there is provided an improved and cost effective process for the preparation of an alkyl 5-[4-[4-(5-cyanoindol-3-yl)butyl]piperazin-1-yl]benzofuran-2-carboxylate of formula II(ii):

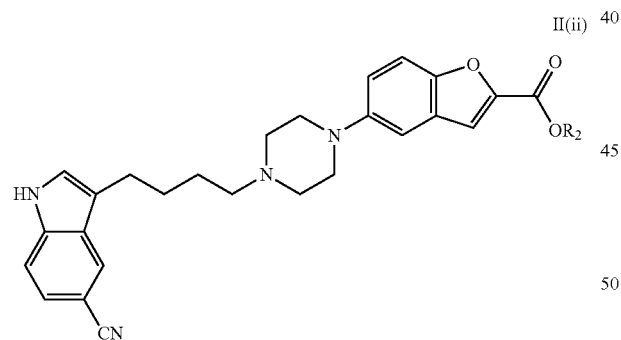

or an acid addition salt thereof, wherein $R_2$ is an alkyl group having 1 to 4 carbon atoms, which comprises reacting a sulfonyl compound of formula VI:

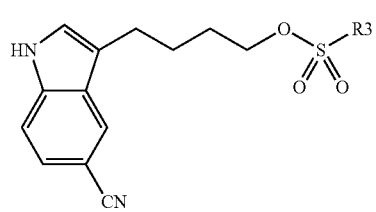

or a salt thereof, wherein 'R3' is an alkyl, cycloalkyl, haloalkyl, aralkyl, or substituted or unsubstituted aryl group; with an alkyl 5-(1-piperazinyl)benzofuran-2-carboxylate compound of formula II(i):

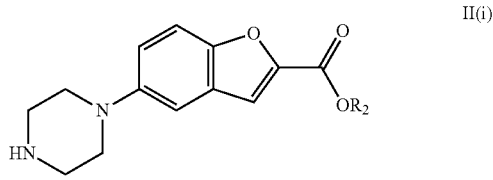

or an acid addition salt thereof, wherein $R_2$ is an alkyl group having 1 to 4 carbon atoms; in the presence of a base in a polar aprotic solvent to produce the alkyl 5-[4-[4-(5-cyanoindol-3-yl)butyl]piperazin-1-yl]benzofuran-2-carboxylate of formula II(ii) or an acid addition salt thereof, wherein the polar aprotic solvent is selected from the group consisting of N,N-dimethylformamide, N,N-dimethylacetamide and dimethylsulfoxide or a combination thereof.

The above process for the preparation of the alkyl 5-[4-[4-(5-cyanoindol-3-yl)butyl]piperazin-1-yl]benzofuran-2-carboxylate of formula II(ii) is carried out by using the methods, reagents and parameters as described hereinabove. In one embodiment, the polar aprotic solvent used is N,N-dimethylformamide.

According to another aspect, there is provided an improved process for the preparation of 3-(4-chlorobutyl)-1H-indole-5-carbonitrile of formula XII:

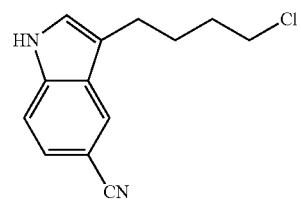

or a salt thereof, comprising reducing 3-(4-chlorobutyryl)-1H-indole-5-carbonitrile of formula XIII:

XIII or a salt thereof, with sodium cyanoborohydride or sodium borohydride in the presence of chlorotrimethylsilane in a suitable solvent to produce the 3-(4-chlorobutyl)-1H-indole-5-carbonitrile of formula XII or a salt thereof.

Exemplary solvents used for reducing the compound of formula XIII described herein include, but are not limited to, an ether, a nitrile, a halogenated hydrocarbon solvent, and mixtures thereof.

Specifically, the solvent is selected from the group consisting of tetrahydrofuran, 2-methyl-tetrahydrofuran, dioxane, diethyl ether, diisopropyl ether, methyl tert-butyl ether, monoglyme, diglyme, acetonitrile, propionitrile, dichloromethane, dichloroethane, and mixtures thereof. A most specific solvent is acetonitrile.

In one embodiment, the reduction is carried out at a temperature of about −10° C. to the reflux temperature of the solvent used, specifically at a temperature of about 0° C. to about 40° C., and more specifically at about 0° C. to about 30° C. The reaction time may vary between about 1 hour to about 20 hours, and most specifically about 6 hours to about 16 hours.

The reaction mass containing the 3-(4-chlorobutyl)-1H-indole-5-carbonitrile of formula XII obtained may be subjected to usual work up methods as described hereinabove.

In one embodiment, the 3-(4-chlorobutyl)-1H-indole-5-carbonitrile of formula XII obtained is isolated and/or recrystallized from a suitable solvent by conventional methods as described hereinabove.

The solvent used for isolating and/or recrystallizing the 3-(4-chlorobutyl)-1H-indole-5-carbonitrile of formula XII is selected from the group consisting of water, methanol, ethanol, isopropanol, dichloromethane, dichloroethane, chloroform, and mixtures thereof.

It has been surprisingly found that the reduction of 3-(4-chlorobutyryl)-1H-indole-5-carbonitrile of formula XIII produces the product with higher yields (above 75%) when sodium cyanoborohydride or sodium borohydride is used as a reducing agent in the presence of chlorotrimethylsilane.

Instrumental Details:
Infra-Red Spectroscopy (FT-IR):
FT-IR spectroscopy was carried out with a Bruker vertex 70 spectrometer. For the production of the KBr compacts approximately 5 mg of sample was powdered with 200 mg of KBr. The spectra were recorded in transmission mode ranging from 3800 $cm^{-1}$ to 650 $cm^{-1}$.
Differential Scanning Calorimetry (DSC):
Differential Scanning calorimetry (DSC) measurements were performed with a Differential Scanning calorimeter (DSC Q200 V23.10 Build 79, Universal V4.4A TA Instruments) equilibrated at 40° C. and Ramp at a scan rate of 10° C. per minute to 210° C.

The following examples are given for the purpose of illustrating the present invention and should not be considered as limitation on the scope or spirit of the invention.

EXAMPLES

Example 1

Preparation of 5-(1-Piperazinyl)benzofuran-2-carboxamide

Step-1: Preparation of Methyl 5-[4-(Benzenesulfonyl)-1-piperazinyl]benzofuran-2-carboxylate Methyl 5-aminobenzofuran-2-carboxylate (200 g) and N-benzenesulfonyl-N,N-bis(2-chloroethyl)amine (289 g) were added to tributyl amine (1012 ml) under stirring at 25-30° C. The resulting mixture was heated to 73-77° C., followed by stirring for 43 hours at the same temperature. The reaction mass was cooled to 25-30° C., followed by the addition of methanol (506 ml) and then stirring for 30 minutes at 25-30° C. The resulting mass was filtered, washed with chilled methanol (200 ml) and then dried to produce 220 g of methyl 5-[4-(benzenesulfonyl)-1-piperazinyl]benzofuran-2-carboxylate as a fine powder (Purity by HPLC: 99.5%).

Step-2: Preparation of Methyl 5-(1-piperazinyl)benzofuran-2-carboxylate Method A Methyl 5-[4-(benzenesulfonyl)-1-piperazinyl]benzofuran-2-carboxylate (10 g) was added to sulfuric acid (25 g) at 25-30° C. and the mixture was heated to 98-102° C., followed by stirring for 15 minutes at the same temperature. The reaction mass was cooled to 25-30° C. and then poured into ice cold water (80 ml). The pH of the resulting aqueous layer was adjusted to 9-10 with ammonium hydroxide solution, followed by extracting with ethyl acetate (3×200 ml) and then distilling off the solvent under vacuum to produce 6.5 g of methyl 5-(1-piperazinyl)benzofuran-2-carboxylate (Yield: 96%).
Method B:
Methyl 5-[4-(benzenesulfonyl)-1-piperazinyl]benzofuran-2-carboxylate (30 g) was added to a solution of hydrobromic acid in acetic acid (180 ml) and 4-hydroxybenzoic acid (24 g). The resulting mixture was stirred for 5 minutes at 25-30° C., followed by heating the mixture to 80-85° C. and maintaining for 6 hours at the same temperature. The reaction mass was poured into methanolic HCl (1000 ml), followed by heating to reflux and then stirring for 6 hours under reflux. The resulting mass was cooled to 0-5° C. and then stirred for 1 hour at the same temperature. The separated solid was filtered and washed with chilled methanol (100 ml). The wet solid was added to methanolic HCl (500 ml) and then heated to reflux for 4 hours. The resulting mass was cooled to 0-5° C. and then stirred for 1 hour at the same temperature. The separated solid was filtered, washed with chilled methanol (100 ml) and then dried at 60-65° C. The resulting solid was added to toluene (500 ml) at 25-30° C., followed by purging ammonia gas slowly for 7 hours. After completion of the ammonia gas purging, the reaction mass was stirred for 15 minutes at 25-30° C. The resulting mass was filtered and the filtrate was distilled to produce 16 g of methyl 5-(1-piperazinyl)benzofuran-2-carboxylate (Purity by HPLC: 99.5%; Yield: 82.5%).

Step-3: Preparation of 5-(1-Piperazinyl)benzofuran-2-carboxamide

Methyl 5-(1-piperazinyl)benzofuran-2-carboxylate (37 g) was added to saturated methanolic ammonia solution (1850 ml) at 25-30° C., the mixture was stirred for 6 to 16 hours at the same temperature. The reaction mass was distilled under vacuum to remove the solvent after completion of the reaction. Water (148 ml) was added to the resulting residue, followed by adjusting the pH to 2-4 with concentrated HCl and then filtering the aqueous layer. The pH of the resulting aqueous layer was adjusted to 9-10 with ammonium hydroxide solution. The separated solid was filtered, washed with water (100 ml) and then dried to produce 25.5 g of 5-(1-piperazinyl)benzofuran-2-carboxamide (Purity by HPLC: 99%; Yield: 73.1%).

Example 2

Preparation of Methyl 5-[4-[4-(5-cyanoindol-3-yl)butyl]piperazin-1-yl]benzofuran-2-carboxylate Step-1: Preparation of 3-(4-Hydroxybutyryl)-1H-indole-5-carbonitrile Aluminium chloride (82.44 g) was added to dichloromethane (350 ml) under stirring at 25-30° C. The resulting mass was cooled to 0-5° C., followed by drop-wise addition of 4-chlorobutyryl chloride (87.5 g) for 30-45 minutes at 0° C. and then stirring for 5 minutes at the same temperature. A solution of 5-cyanoindole (50 g) in dichloromethane (350 ml) was added drop-wise to the resulting mass at 0-5° C. within 1-2 hours, followed by stirring for 30 minutes at the same temperature. The temperature of the reaction mass was gradually increased to 25-30° C., followed by stirring for 12-16 hours at the same temperature. The reaction mass was slowly poured into crushed ice (420 g) with slow stirring, the resulting mixture was cooled to 0-5° C. and then stirred for 1 hour at the same temperature. The separated solid was filtered, washed the material subsequently with dichloromethane (2×85 ml) and water (2×85 ml) and then dried at 25-30° C. to produce a solid material (Dry weight: 93 g). The resulting solid was added to 50% aqueous methanol (2500 ml) at 25-30° C., followed by heating to reflux and stirring for 2 to 3 hours at reflux. Activated carbon (10 g) was added to the reaction mass at reflux temperature and then stirred for 5 minutes at the same temperature. The resulting mixture was filtered through celite bed and washed the bed with hot 50% aqueous methanol (100 ml). The resulting filtrate was initially cooled to 25-30° C. and further cooled to 0-5° C., followed by maintaining for 1 hour at the same temperature. The separated solid was filtered, washed with chilled 50% aqueous methanol (50 ml) and then dried at 60-65° C. until constant weight to produce 59.5 g of pure 3-(4-hydroxybutyryl)-1H-indole-5-carbonitrile as a white crystalline solid (Purity by HPLC: 99%; Yield: 74.1%).

Analytical Data:
Melting Point: 176° C. (measured by DSC); Infra-red (FT-IR) Data (KBr pellet): 3525 cm$^{-1}$ (—OH), 3151 cm$^{-1}$ (—NH), 2861-2957 cm$^{-1}$ (—CH$_2$), 2221 cm$^{-1}$ (—CN), 1626 cm$^{-1}$ (—C═O), 1615 cm$^{-1}$ (—C═C, Ar); and Mass (m/z): 229 (M+1).

Step-2: Preparation of 3-(4-Hydroxybutyl)-1H-indole-5-carbonitrile 3-(4-Hydroxybutyryl)-1H-indole-5-carbonitrile (50 g) was added to acetonitrile (750 ml) at 25-30° C., followed by the addition of sodium cyanoborohydride (75 g) at the same temperature. The resulting mixture was cooled to 0-5° C., followed by drop-wise addition of a mixture of concentrated HCl (112.5 ml) and water (112.5 ml) for a period of 15 minutes at the same temperature. After completion of the reaction, water (750 ml) was added to the reaction mass at 0-5° C., followed by stirring for 5 minutes at the same temperature. The layers were separated and the aqueous layer was extracted two times with toluene (2×1000 ml). The resulting organic layers were combined, washed two times with water (2×1000 ml), and then distilled off the solvent under vacuum to produce 42 g of the titled compound as a residue. Dichloromethane (420 ml) was added to the residue at 25-30° C. to form a clear solution, followed by filtration to remove undissolved particles. The resulting filtrate was cooled to −5° C. to 0° C. and then stirred for 1-2 hours at the same temperature. The separated solid was filtered, washed with chilled dichloromethane (42 ml) and then dried at 50-55° C. to produce 31 g of 3-(4-hydroxybutyl)-1H-indole-5-carbonitrile (Purity by HPLC: 99%). The mother liquors were taken and distilled off the solvent under vacuum to give 11 g of the titled compound as a residue (Total yield: 86%).

Step-3: Preparation of 3-[4-(p-toluenesulfonyloxy) butyl]-1H-indole-5-carbonitrile 3-[4-(p-Toluenesulfonyloxy)butyl]-1H-indole-5-carbonitrile was prepared by reacting 3-(4-hydroxybutyl)-1H-indole-5-carbonitrile with p-toluenesulfonyl chloride in the presence of base in dichloromethane as per the process exemplified in example 2 of Chinese Patent Application Publication No. CN 102267932 A.

Step-4: Preparation of Methyl 5-[4-[4-(5-cyanoindol-3-yl)butyl]piperazin-1-yl]benzofuran-2-carboxylate Methyl 5-(1-piperazinyl)benzofuran-2-carboxylate (5 g), 3-[4-(p-toluenesulfonyloxy) butyl]-1H-indole-5-carbonitrile (6.3 g) and triethylamine (7 ml) were added to dimethylformamide (6.3 ml) and the resulting mixture was heated to 77-82° C., followed by stirring for 45 minutes at the same temperature. Water (30 ml) was added to the reaction mass and then stirred for 5 minutes at 25-30° C. The separated aqueous layer was extracted two times with toluene (2×250 ml). The resulting organic layers were combined and then washed two times with water (2×250 ml) and then distilled off the solvent under vacuum to produce 9.5 g of the titled compound as a residue. Methanol (47.5 ml) was added to the residue at 25-30° C. and then stirred for 30 minutes at the same temperature. The separated solid was filtered, washed with chilled methanol (10 ml) and then dried the material at 70-75° C. to produce 6 g of Methyl 5-[4-[4-(5-cyanoindol-3-yl)butyl]piperazin-1-yl]benzofuran-2-carboxylate (Purity by HPLC: 99%; Yield: 76.9%).

Example 3

Preparation of 3-(4-Chlorobutyl)-1H-indole-5-carbonitrile

Step-1: Preparation of 3-(4-Chlorobutyryl)-1H-indole-5-carbonitrile

Aluminium chloride (82.44 g) was added to dichloromethane (350 ml) under stirring at 25-30° C. The resulting mass was cooled to 0-5° C., followed by drop-wise addition of 4-chlorobutyryl chloride (87.5 g) for 30-45 minutes at 0° C. and then stirring for 5 minutes at the same temperature. A solution of 5-cyanoindole (50 g) in dichloromethane (350 ml) was added drop-wise to the resulting mass at 0-5° C. within 1-2 hours, followed by stirring for 30 minutes at the same temperature. The temperature of the reaction mass was gradually increased to 25-30° C., followed by stirring for 12-16 hours at the same temperature. The reaction mass was slowly poured into crushed ice (420 g) with slow stirring, the resulting mixture was cooled to 0-5° C. and then stirred for 1 hour at the same temperature. The separated solid was filtered, washed the material subsequently with dichloromethane (2×85 ml) and water (2×85 ml) and then dried at 25-30° C. to produce a solid material (Dry weight: 93 g). The resulting solid was dissolved in ethyl acetate (4000 ml) at 50-55° C., followed by the addition of activated carbon (5 g) and then stirring the mixture for 5 minutes at the same temperature. The resulting mass was filtered through celite bed and washed the bed with hot ethyl acetate (100 ml). The resulting filtrate was initially cooled to 25-30° C. and further cooled to 0-5° C., followed by stirring the mass for 1 hour at the same temperature. The separated solid was filtered, washed with chilled ethyl acetate (100 ml) and then dried the material at 50-55° C. until constant weight to produce 65 g of 3-(4-chlorobutyryl)-1H-indole-5-carbonitrile (Purity by HPLC: 99.2%; Yield: 74.8%).

Step-2: Preparation of 3-(4-Chlorobutyl)-1H-indole-5-carbonitrile

Chlorotrimethylsilane (137 g) was added to a mixture of 3-(4-chlorobutyryl)-1H-indole-5-carbonitrile (50 g) and acetonitrile (750 ml) at 25-30° C. The resulting mixture was cooled to 0° C., followed by portion wise addition of sodium cyanoborohydride (75 g) while maintaining the temperature at 0-5° C. during the time period of 30 minutes to 1 hour. The resulting mass was stirred for 1 hour at the same temperature. The temperature of the reaction mass was then raised to 25-30° C., followed by stirring for 6-16 hours at the same temperature. The reaction mass was slowly poured into water (5 Lt) at 25-30° C. and then stirred for 30 minutes to 1 hour at the same temperature. The separated solid was filtered and then dissolved in dichloromethane (900 ml) and the resulting organic layer was washed with 20% sodium chloride solution (400 ml×10). The resulting organic layer was subjected to carbon treatment, followed by distillation of the organic layer at 50-55° C. under vacuum to produce the titled compound as a residue. The resulting residue was dissolved in 5% aqueous methanol (4 to 5 times to the weight of the residue), followed carbon treatment at 50-55° C. The resulting filtrate was finally cooled to 25-30° C., the separated solid was filtered, washed with chilled 5% aqueous methanol (50 ml) and then dried the material at 60-65° C. to produce 31 g of 3-(4-chlorobutyl)-1H-indole-5-carbonitrile (First Crop). The resulting filtrate was cooled to 0-5° C. and then stirred for 30 minutes at the same temperature. The separated solid was filtered, washed with chilled 5% aqueous methanol and then dried the material at 60-65° C. to produce 10.5 g of the titled compound (Second Crop) (Purity by HPLC: 99.3; Total yield: 87.2%).

Example 4

Preparation of 5-[4-[4-(5-Cyanoindol-3-yl)butyl]piperazin-1-yl]benzofuran-2-carboxamide (Vilazodone)

Methyl 5-[4-[4-(5-cyanoindol-3-yl)butyl]piperazin-1-yl]benzofuran-2-carboxylate (41 g) was added to saturated methanolic ammonia solution (8200 ml) under stirring at 25-30° C., the resulting mixture was stirred for 3 to 4 hours at the same temperature to form a clear solution. The reaction mass was stirred for 24 hours at 25-30° C., followed by filtration of the separated solid and then dried to produce 28 g of vilazodone. The mother liquors were taken and the solvent was distilled off under vacuum until the solvent quantity reaches around 1200 ml of the initial volume. The resulting mass was cooled to 25-30° C., followed by filtration and then drying to produce 11 g of Vilazodone (Purity by HPLC: 99.5%; Yield: 98.5%).

Example 5

Preparation of Vilazodone

Methyl 5-[4-[4-(5-cyanoindol-3-yl)butyl]piperazin-1-yl]benzofuran-2-carboxylate (41 g) was taken in methanol (1000 ml) under stirring at 25-35° C., followed by reacting with ammonia gas for 2 hours under pressure of 4 Kg/cm². The separated solid was filtered and then dried to produce 32 g of vilazodone. The mother liquors were taken and the solvent was distilled off under vacuum until the solvent quantity reaches around 50 ml of the initial volume. The resulting mass was cooled to 25-30° C., followed by filtration and then drying to produce 6 g of Vilazodone (Purity by HPLC: 99.5%; Yield: 96%).

Example 6

Preparation of Vilazodone Hydrochloride

Vilazodone hydrochloride (1 g) was dissolved in methanol (400 ml) at 60° C. and the resulting solution was subjected to carbon treatment by stirring the solution with activated carbon (0.4 g) for 10 minutes at 58-62° C. The resulting mixture was filtered through a hyflo bed and the resulting filtrate was cooled to 25-30° C. and then subjected to spray-drying in a mini spray dryer (Buchi model-290) at an inlet temperature of about 78-81° C. and an outlet temperature of about 45-53° C., and flow rate of 16.8 ml/minute using nitrogen gas to produce 0.75 g of amorphous Vilazodone hydrochloride as a white powder (Purity by HPLC: 99.73%).

All ranges disclosed herein are inclusive and combinable. While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

We claim:

1. A process for preparing an alkyl 5-(1-piperazinyl)benzofuran-2-carboxylate compound of formula II(i):

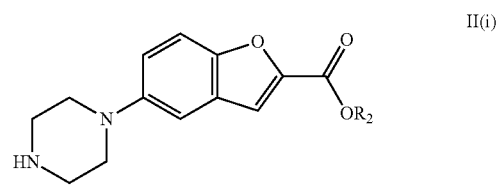

II(i)

or an acid addition salt thereof, wherein $R_2$ is an alkyl group having 1 to 4 carbon atoms, comprising:

a) reacting an alkyl 5-aminobenzofuran-2-carboxylate compound of formula III:

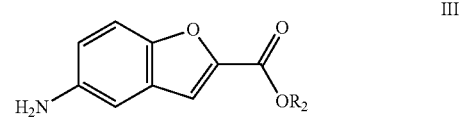

III or an acid addition salt thereof, wherein $R_2$ is as defined in formula II(i);

with a sulfonamide compound of formula IV:

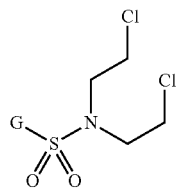

wherein G is selected from alkyl, cycloalkyl, and a phenyl radical which is unsubstituted or substituted by alkyl, alkoxy, halo, nitro, amino or acetyl amino group;

in the presence of a base to produce a sulfonyl piperazine compound of formula V:

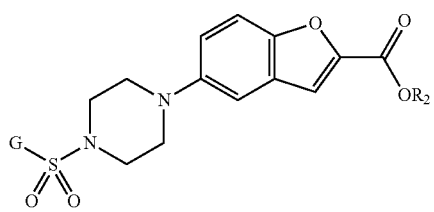

wherein G and $R_2$ are as defined above; and b) deprotecting the compound of formula V to produce the alkyl 5-(1-piperazinyl)benzofuran-2-carboxylate compound of formula II(i), and optionally converting the compound of formula II(i) obtained into an acid addition salt thereof.

2. The process of claim 1, wherein the group '$R_2$' in the compounds of formulae II(i), III and V is selected from methyl, ethyl, n-propyl, isopropyl, n-butyl, sec-butyl and tert-butyl; and wherein the group 'G' in the compounds of formulae IV and V is selected from methyl, ethyl, cyclohexyl, phenyl, tolyl, methoxy substituted phenyl, chloro substituted phenyl and nitro substituted phenyl.

3. The process of claim 2, wherein the group $R_2$ is methyl or ethyl; and wherein the group G is methyl, phenyl or p-tolyl.

4. The process of claim 1, wherein the reaction in step-(a) is carried out in the presence or absence of a reaction inert solvent; wherein the base used in step-(a) is an organic or inorganic base; and wherein the base in step-(a) is used as both solvent and acid scavenger.

5. The process of claim 4, wherein the reaction in step-(a) is carried out in the presence of a reaction inert solvent selected from the group consisting of water, an alcohol, a ketone, a chlorinated hydrocarbon solvent, an ester, an ether, a polar aprotic solvent, and mixtures thereof; and wherein the base used in step-(a) is an organic base selected from the group consisting of trimethylamine, tributylamine, triethylamine, dibutylamine, diisopropylethylamine, N-methylmorpholine, N-ethylmorpholine, 4-(N,N-dimethylamino)pyridine, N,N-dimethylaniline and 1-alkylimidazole.

6. The process of claim 1, wherein the deprotection reaction in step-(b) is carried out in the presence of an acid, wherein the acid is an organic acid or an inorganic acid or a combination thereof; wherein the deprotection reaction in step-(b) is carried out in the presence or absence of a reaction inert solvent; and wherein the acid employed for deprotection is also used as solvent.

7. The process of claim 6, wherein the acid is selected from the group consisting of the hydrochloric acid, hydrobromic acid, sulfuric acid, nitric acid, oxalic acid, acetic acid, propionic acid, phosphoric acid, 4-hydroxybenzoic acid, or a combination thereof; and wherein the deprotection reaction in step-(b) is carried out in the presence of a reaction inert solvent selected from the group consisting of water, an alcohol, a ketone, a chlorinated hydrocarbon solvent, an ester, an ether, a polar aprotic solvent, and mixtures thereof.

\* \* \* \* \*